(12) United States Patent
Grebe

(10) Patent No.: US 9,921,229 B2
(45) Date of Patent: *Mar. 20, 2018

(54) IMMUNOCHROMATOGRAPHY DEVICES, METHODS, AND KITS

(71) Applicant: Grifols Therapeutics, Inc., Research Triangle Park, NC (US)

(72) Inventor: Marco Grebe, Frankfurt am Main (DE)

(73) Assignee: Grifols Therapeutics Inc., Research Triangle Park, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/803,416

(22) Filed: Jul. 20, 2015

(65) Prior Publication Data

US 2015/0323526 A1 Nov. 12, 2015

Related U.S. Application Data

(62) Division of application No. 13/823,505, filed as application No. PCT/IB2011/002232 on Sep. 23, 2011, now Pat. No. 9,121,857.

(60) Provisional application No. 61/386,214, filed on Sep. 24, 2010, provisional application No. 61/482,867, filed on May 5, 2011.

(51) Int. Cl.
| | |
|---|---|
| *G01N 33/558* | (2006.01) |
| *G01N 33/68* | (2006.01) |
| *C07K 16/38* | (2006.01) |
| *G01N 33/543* | (2006.01) |

(52) U.S. Cl.
CPC ......... *G01N 33/6893* (2013.01); *C07K 16/38* (2013.01); *G01N 33/54366* (2013.01); *G01N 33/54386* (2013.01); *G01N 33/558* (2013.01); *G01N 2333/8125* (2013.01)

(58) Field of Classification Search
CPC ......... G01N 2333/8125; G01N 33/558; G01N 2400/00; G01N 33/54366; G01N 2021/7759; C07K 16/38
See application file for complete search history.

(56) References Cited

U.S. PATENT DOCUMENTS

| | | |
|---|---|---|
| 2003/0032196 A1 | 2/2003 | Zhou |
| 2003/0092090 A1 | 5/2003 | Hajizadeh |
| 2006/0246513 A1 | 11/2006 | Bohannon |

FOREIGN PATENT DOCUMENTS

| | | |
|---|---|---|
| EP | 2 317 319 A1 | 1/2010 |
| JP | 11201969 A | 7/1999 |
| WO | WO 01/13111 A2 | 2/2001 |
| WO | WO 2010/001598 A1 | 1/2010 |
| WO | WO 2010/089102 A1 | 8/2010 |

OTHER PUBLICATIONS

Boneberger et al. (IVD Technology, published May 1, 2006, retrieved from http://www.ivdtechnology.com/print/754).
European Search Report in application No. 11826474.6, dated Feb. 24, 2014.
Gershagen, S. et al. ELISA for specific detection of PiZ-related alpha1-antitrypsin deficiency. Clin. Chem., 2004, vol. 50, No. 12, pp. 2407-2410.
Janciauskiene, S. et al. Detection of circulating and endothelial cell polymers of Z and wild type alpha1-antitrypsin by a monoclonal antibody. J. Biol. Chem., 2002, vol. 277, No. 29, pp. 26540-26546.
Millipore Guide (2002; retrieved from (http://www.millipore.com/publications.nsf/a73664f9f981af8c852569b9005b4eee/348ee7096d93729b85256bf40066a40d/$FILE/tb500en00.pdf.
Sergi, C. et al. Immunohistochemical and genetic characterization of the M Cagliari alpha-1-antitrypsin molecule (M-like alpha-1-antitrypsin deficiency). Lab. Invest., 1994, vol. 70, No. 1, pp. 130-133.
Sten Eriksson et al.; "Lack of Association between Hemochromatosis and [alpha]-Antitrypsin Deficiency"; Acta Medica Scaninavica; vol. 219, No. 3, Jan. 12, 1986, pp. 291-294, XP055103724.
Wallmark, A. et al.; Monoclonal antibody specific for the mutant PiZ alpha 1-antitrypsin and its application in an ELISA procedure for identification of PiZ gene carriers, Proc Natl Acad Sci USA, 1984, vol. 84, No. 18, pp. 5690-5693.

*Primary Examiner* — Tracy Vivlemore
*Assistant Examiner* — Carmencita M Belei
(74) *Attorney, Agent, or Firm* — Dinsmore & Shohl LLP

(57) ABSTRACT

A membrane-based assay device, methods and kits for determining the presence or quantity of an analyte in a test sample are provided. The immunochromatographic device comprises a membrane having a capture antibody bound thereto at a test zone, wherein the capture antibody is capable of binding with an analyte, in particular a Z-AAT protein present in a sample from a PiZ gene carrier.

13 Claims, 31 Drawing Sheets

IMMUNOCHROMATOGRAPHY DEVICES, METHODS, AND KITS

RELATED APPLICATIONS

This application is a Divisional application of U.S. application Ser. No. 13/823,505 filed on Mar. 14, 2013, which is a U.S. national phase application of PCT/IB2011/002232 filed Sep. 23, 2011, which claims priority to U.S. Provisional Application No. 61/386,214 filed Sep. 24, 2010, and to U.S. Provisional Application No. 61/482,867 filed May 5, 2011, each of which is incorporated by reference in its entirety herein.

FIELD OF THE INVENTION

The present invention relates to devices and assays involving specific binding, in particular immunochromatographic devices and assays.

BACKGROUND

Various analytical procedures and devices are commonly employed in flow-through assays to determine the presence and/or concentration of analytes that may be present in a test sample. Lateral flow tests, also known as lateral flow immunochromatographic assays or lateral flow assays (LFAs), are commonly used in point-of-care (POC) devices for medical diagnostics, for example. Individual assay layouts are adapted to a particular application.

Alpha-1 Antitrypsin Deficiency (AATD) is a hereditary disease, which can be diagnosed by genetic testing. However, AATD is under-diagnosed and only 10-15% are identified. Unidentified patients are sometimes misdiagnosed as "usual" chronic obstructive pulmonary disease (COPD) and Asthma, respectively.

A need still exists for an effective lateral flow assay for determining the presence of an analyte, in particular a Z-AAT protein.

SUMMARY OF THE INVENTION

In one aspect, the present invention provides an immunochromatographic device comprising a membrane having a capture antibody bound thereto at a test zone. The capture antibody is capable of binding with an analyte. The analyte can be a Z-AAT protein present in a sample from a PiZ gene carrier.

In some aspects, the present invention provides an immunoassay device comprising: a membrane having a Z-AAT protein capture area defined by a capture antibody immobilized thereto, wherein the capture antibody is an anti-Z-AAT protein antibody.

In other aspects, the present invention provides an immunoassay device for determining the presence or amount of a Z-AAT protein in a fluid sample. The device comprises:
a sample application area;
a microporous membrane having a Z-AAT protein capture area defined by a capture antibody immobilized thereto, wherein the capture antibody is LG96 or antigen-binding fragment thereof;
a flow path from the sample application area to the Z-AAT protein capture area, wherein the presence or amount of a Z-AAT protein in a fluid sample can be determined by formation of a complex between the capture antibody and the Z-AAT protein that may be present in the fluid sample; and
a conjugate structure located in the flow path, wherein the conjugate structure comprises a detection reagent specific for the Z-AAT protein, the detection reagent being mobile or mobilizable, wherein the detection reagent is gold-conjugated LG96 or a gold-conjugated antigen-binding fragment thereof.

In one aspect, a method for detecting a Z-AAT protein in a subject is provided. The method comprises:
applying a biological sample from the subject to the immunoassay device of present invention; and
detecting a complex that is formed between the capture antibody and the Z-AAT protein that may be present in the fluid sample, wherein detection of the complex indicates the presence of the Z-AAT protein in the sample.

In another aspect, the present invention provides a method for determining a PiZ gene carrier. The method comprises subjecting a sample from a subject to immunochromatography using a device in accordance with the present invention; and determining binding of an analyte to a capture antibody, wherein binding of the analyte to the capture antibody indicates that the subject is a PiZ carrier.

In some aspects, the present invention provides a method for diagnosing a condition or disease associated with AAT deficiency. The method comprises subjecting a sample from a subject to immunochromatography using a device in accordance with the present invention; and determining binding of an analyte to a capture antibody, wherein binding of the analyte to the capture antibody indicates that the subject has the condition or disease.

In other aspects, the present invention provides a method for determining a subject's predisposition to developing a condition or disease associated with AAT deficiency. The method comprises subjecting a sample from a subject to immunochromatography using a device in accordance with the present invention; and determining binding of an analyte to a capture antibody, wherein binding of the analyte to the capture antibody is indicative of the subject's predisposition to developing the condition or disease.

In one aspect, the present invention provides a method for determining the presence of a Z-AAT protein in a biological sample. The method comprises: providing the biological sample and a first antibody in a mixed state on a membrane having a second antibody bound thereto at a test zone, wherein each of the first and the second antibody is capable of binding to the Z-AAT protein; wherein capture of the second antibody at the test zone indicates the presence of the Z-AAT protein in the sample.

In still further aspects, the present invention provides a kit comprising a device in accordance with the present invention; and a detection reagent.

DETAILED DESCRIPTION OF THE INVENTION

Figure 1:
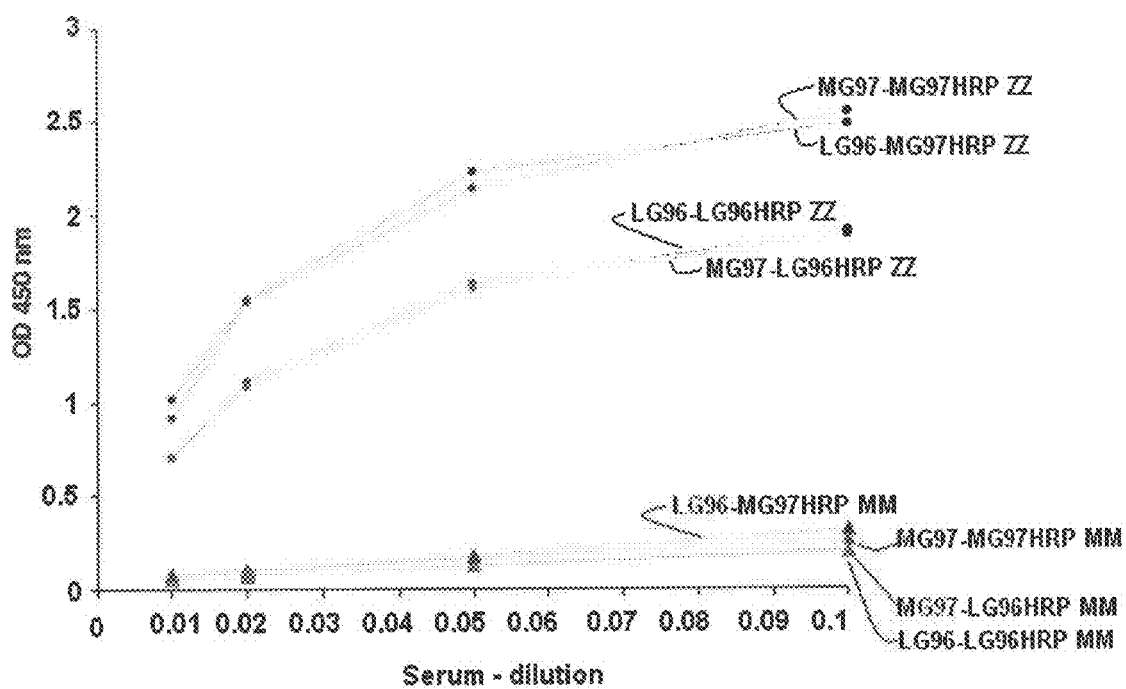
FIG. 1 shows the results of testing of matching pairs, sandwich-ELISA with monoclonal antibodies LG96 and MG97. Partially purified monoclonal antibodies LG96 and MG97 were either used as capture antibodies or used as detector antibodies labeled with horseradish-peroxidase (LG96HRP or MG97HRP respectively). Pooled ZZ- or MM-serum were serial-diluted with Sample Buffer and used as antigen solution. The matching pairs LG96-LG96HRP, LG96-MG97HRP, MG97-LG96HRP and MG97-MG97HRP show specific binding with PiZZ-serum but not with PiMM-serum.

In one aspect, the present invention provides an immunochromatographic device comprising a membrane having a capture antibody bound thereto at a test zone. The capture antibody is capable of binding with an analyte. In the preferred embodiment, the analyte is a Z-AAT protein. The device can be used to determine the presence of the analyte in a sample.

The term "Z-AAT protein," as used herein refers to a Z-AAT polymer(s) of amino acids and is not intended to refer to a specific length of the protein; thus, fragments thereof are included within the definition of "Z-AAT protein." This term also includes forms, variants, and analogues of the Z-AAT protein including monomers, dimers, multimers, etc. as well as post-translational modifications of the protein, for example, glycosylations, acetylations, phosphorylations and the like. Thus, in some embodiments, the term "Z-AAT protein" may be synonymous with the term "Z-AAT polypeptide" or may refer to a complex of two or more Z-AAT polypeptides (e.g., dimeric, multimeric, aggregated).

Sample

The sample, generally, refers to a material that may or may not contain the analyte. The sample can be used directly as obtained from a source or following a pretreatment to modify or alter a characteristic of the sample. The source of the sample can be any biological source, such as a physiological fluid, including, but not limited to, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. Preferably, the sample is an aqueous sample.

In some embodiments, the sample is an undiluted sample i.e., the sample is obtained from the biological source and applied directly to the device without any pre-dilution of the sample. In other embodiments, the sample is pretreated prior to use, such as preparing plasma from blood, diluting viscous fluids, and the like. Pre-treatment of the sample can involve filtration, precipitation, dilution, distillation, concentration, inactivation of interfering components, and the addition of reagents. In one embodiment, a solid material suspected of containing the analyte can be used as the source of the sample, preferably by modifying the solid material to form a liquid or semi-liquid composition.

In one embodiment, the sample is whole blood, plasma, or serum. In another embodiment, the sample is capillary blood.

Membrane

The device of the present invention provides a membrane-based immunochromatographic assay for determining the presence or quantity of the analyte in the sample. In preferred embodiments, the analyte is a Z-AAT protein. For example, in one embodiment, the analyte is a Z-AAT protein, wherein the presence of the analyte in a sample of blood obtained from a mammal (e.g., human) indicates that the mammal is a PiZ gene carrier.

The membrane can be made from any of a variety of materials through which the sample is capable of passing. For example, the materials used to form the membrane can include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; nylon membranes; silica; inorganic materials, such as deactivated alumina, diatomaceous earth, MgS0, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like.

In one embodiment, the membrane is formed from nitrocellulose and/or polyester sulfone materials. The nitrocellulose can be nitric acid esters of cellulose, which may be nitrocellulose alone, or a mixed ester of nitric acid and other acids, such as aliphatic carboxylic acids having one or more carbon atoms.

In some embodiments, the membrane comprises nitrocellulose. Nitrocellulose can have the ability to bind proteins without requiring prior sensitization. Certain reagents, such as antibodies, can be applied directly to nitrocellulose and immobilized thereon. Little or no chemical treatment is required which might interfere with the essential specific binding activity of the reagent. Unused binding sites on the nitrocellulose can thereafter be blocked using simple materials, such as polyvinyl alcohol. Moreover, nitrocellulose is readily available in a range of pore sizes and this facilitates the selection of a membrane material to suit particularly requirements such as sample flow rate, etc.

In one embodiment, the membrane comprises a single test zone or line or region having the capture antibody bound thereto.

In other embodiments, the membrane comprises a plurality of test zones arranged, e.g. in series, on the membrane, through which the aqueous sample can pass progressively. In one embodiment, the plurality of test zones can be used to provide a quantitative measurement of the analyte, or, in another embodiment, can be loaded individually with different specific capture antibodies to provide a multi-analyte test.

In still further embodiments, the membrane comprises a control zone to provide a determination that the device has worked. Preferably, the control zone is located downstream from the test zone(s) at which the desired test result is determined. A positive control indicator therefore provides information that the sample at least has permeated the required distance through the membrane.

For example, the control zone can be loaded with an antibody or other molecule/reagent that will bind to a detection reagent to confirm that the sample has sufficiently permeated the membrane. For example, where the detection reagent is a labeled antibody derived from a murine hybridoma, the control zone can comprise an "anti-mouse" antibody (e.g., anti-mouse IgG). In another embodiment, the control zone can contain an anhydrous reagent that, when moistened, produces a colour change or colour formation, e.g. anhydrous copper sulphate which will turn blue when moistened by an aqueous sample. As a still further embodiment, a control zone can contain immobilized analyte (e.g., Z-AAT protein) that will react with excess detection reagent.

In one embodiment, the membrane comprises a control zone having a control antibody bound thereto, wherein the control antibody is capable of binding with the detection reagent. In some embodiments, the control antibody is an anti-mouse IgG.

Capture Antibody

In preferred embodiments, the capture antibody that is bound to the membrane at the test zone is an antibody, or antigen-binding fragment thereof, that is specific for the Z-AAT protein.

The antibody, in various embodiments, exhibits substantially little or no cross-reactivity to PiMM sera or purified wild type AAT.

In one embodiment, the antibody or an antigen-binding fragment thereof is a monoclonal antibody or antigen-binding fragment thereof.

The terms "polyclonal" and "monoclonal" refer to the degree of homogeneity of an antibody preparation, and are not intended to be limited to particular methods of production. The term "monoclonal antibody" or "monoclonal antibody composition", as used herein, refers to a population of antibody molecules that contain only one species of an antigen-binding site capable of immunoreacting with a particular epitope.

Fragments of antibodies include, but are not limited to, single-chain, chimeric, humanized, primatized, or veneered antibodies also are contemplated. For example, antibody fragments capable of specifically binding to the Z-AAT protein can include, but are not limited to, Fab', Fab, F(ab')$_2$, single domain antibodies (DABs), Fv, scFv (single chain Fv), linear antibodies, diabodies, camelized antibodies and the like. The techniques for preparing and using various antibody-based constructs and fragments are well known in the art. Such fragments can be produced by enzymatic cleavage or by recombinant techniques. For example, papain or pepsin cleavage can generate Fab or F(ab')2 fragments, respectively. Other proteases with the requisite substrate specificity can also be used to generate Fab or F(ab')2 fragments. Antibodies also can be produced in a variety of truncated forms using antibody genes in which one or more stop codons have been introduced upstream of the natural stop site. For example, a chimeric gene encoding a F(ab')2 heavy chain portion can be designed to include DNA sequences encoding the CHi domain and hinge region of the heavy chain.

Single chain antibodies, and chimeric, humanized or primatized (complementary determining region-grafted (CDR-grafted)), or veneered antibodies, as well as chimeric, CDR-grafted or veneered single chain antibodies, comprising portions derived from different species, and the like are also encompassed by the present invention. The various portions of these antibodies can be joined together chemically by conventional techniques, or can be prepared as a contiguous protein using genetic engineering techniques.

In one embodiment, the capture antibody is monoclonal antibody LG96, MG97, or an antigen-binding fragment thereof. In one embodiment, the capture antibody is monoclonal antibody MG97 and the detector antibody is monoclonal antibody LG96. In one embodiment, the capture antibody is monoclonal antibody LG96 and the detector antibody is monoclonal antibody LG96.

Representative sample cells of hybridoma cell lines that produce the monoclonal antibodies LG96 and MG97 were deposited on Sep. 14, 2010 at the "Deutsche Sammlung von Mikroorganismen und Zellkulturen GmbH," Mascheroder Weg Ib, 38124 Braunschweig, Germany under the terms of the Budapest Treaty under Accession Nos. DSM ACC3092 and DSM ACC3093, respectively.

One of ordinary skill in the art can determine nucleic acid sequences of monoclonal antibodies using a number of techniques known in the art. The monoclonal antibody-encoding nucleic acids may be cloned to prepare a "recombinant" monoclonal antibody. Any recombinant cloning technique may be utilized, including the use of the polymerase chain reaction (PCR) to prime the synthesis of the antibody-encoding nucleic acid sequences. Thus, monoclonal antibody preparation methods include methods comprising obtaining at least a first suitable anti-Z-AAT antibody-encoding nucleic acid molecule or segment from a suitable anti-Z-AAT antibody-producing cell, preferably a hybridoma; and expressing the nucleic acid molecule or segment in a recombinant host cell to obtain a recombinant anti-Z-AAT monoclonal antibody.

Other recombinant techniques are known in the art, such as, for example, phagemid library-based methods. For example, the method can comprise: (a) immunizing an animal by administering to the animal at least one dose, and optionally more than one dose, of a composition comprising an immunogenically effective amount of an immunogenic Z-AAT protein, preferably a composition comprising activated endothelial cells; (b) preparing a combinatorial immunoglobulin phagemid library expressing RNA isolated from the antibody-producing cells, preferably from the spleen, of the immunized animal; (c) selecting from the phagemid library at least a first clone that expresses at least a first anti-Z-AAT antibody, optionally one that substantially cross-reacts or competes with the monoclonal antibody LG96 or MG97; (d) obtaining anti-Z-AAT antibody-encoding nucleic acids from the at least a first selected clone and expressing the nucleic acids in a recombinant host cell to provide the at least a first anti-Z-AAT antibody; and (e) obtaining the at least a first anti-Z-AAT antibody expressed by the nucleic acids obtained from the at least a first selected clone.

In some embodiments, the capture antibody that is bound to the membrane at the test zone is an antibody or antigen-binding fragment thereof that is specific for the Z-AAT protein, wherein the antibody or antigen-binding fragment comprises one or more complementary determining regions (CDRs) from monoclonal antibody LG96, MG97, or both.

In another embodiment, the antibody or antigen-binding fragment has the same or similar epitopic specificity as monoclonal antibody LG96 or MG97. Antibodies or antigen-binding fragments with an epitopic specificity that is the same as, or similar to, that of monoclonal antibody LG96 or MG97 can be identified by a variety of methods known in the art. For example, an antibody with the same or similar epitopic specificity can be identified based upon the ability to compete with the monoclonal antibody for binding to a Z-AAT polypeptide. In another example, the binding of, e.g., LG96 mAb, and the binding of an antibody with the same or similar epitopic specificity for a Z-AAT polypeptide can be inhibited by a single peptide (e.g., a natural peptide, a synthetic peptide).

Without being held to any one particular theory, it is believed that a problem with high analyte concentrations in a sample to be tested can be the so-called "Hook effect," which is understood by one of ordinary skill in the art as a decrease of the detectable signal at very high analyte concentrations. Normally, in a heterogeneous sandwich assay format, the soluble labeled antibody (e.g., detection reagent) and the solid phase antibody (e.g., capture antibody) are present in an excess relative to the analyte to be determined so that the sandwich complexes can be formed and also detected essentially completely. However, in the presence of a high analyte concentration, a limited number of antibodies are faced by a very large number of analyte molecules that may be present in the sample. In the extreme case, there is a deficit of solid phase antibody such that the analyte is only partially bound and, moreover, the fraction of analyte bound to the solid phase cannot be completely detected because the labeled antibody is captured by the excess of analyte with formation of complexes of soluble detection antibody/analyte. This can result in a reduction of the measured signal which may lead to a false negative test result.

In some embodiments, the sample is a prediluted sample, which is then subjected to the immunochromatography.

In other embodiments, the membrane comprises one or more capture zones arranged (e.g. in series) on the membrane each at a position proximal to the test zone(s), through which the aqueous sample can pass progressively prior to reaching the test zone(s). In some embodiments, the one or more capture zone(s) comprise monoclonal antibody LG96 or MG97 immobilized/bound thereto. The one or more capture zone(s) can provide for preventing, reducing, or eliminating the Hook effect in assays of samples potentially subject to such an effect.

Conjugate Structure

In one embodiment, the device further comprises a conjugate structure having a detection reagent, such as a detector antibody labeled with a reporter moiety. In some embodiments, the conjugate structure is placed in contact with the membrane, wherein when a liquid is contacted with the conjugate structure; the detection reagent is re-hydrated and carried through the membrane.

In other embodiments, the conjugate structure is fluidly coupled to the membrane at a proximal end of the membrane.

In another embodiment, the conjugate structure is a conjugate pad that partially overlays the membrane at the proximal end of the membrane.

For example, in some embodiments, the conjugate structure is made from a bibulous, porous or fibrous material capable of absorbing liquid rapidly. The porosity of the material can be unidirectional (e.g., with pores or fibres running wholly or predominantly parallel to an axis of the structure) or multidirectional (e.g., omnidirectional, so that the member has an amorphous sponge-like structure). Porous plastics material, such as polypropylene, polyethylene, polyvinylidene flouride, ethylene vinylacetate, acrylonitrile and polytetrafluoroethylene can be used. It can be advantageous to pre-treat the material with a surface-active agent during manufacture, as this can reduce any inherent hydrophobicity in the material and therefore enhance its ability to take up and deliver a moist sample rapidly and efficiently. Porous structure can also be made from paper or other cellulosic materials, such as nitrocellulose. In some embodiments, materials that are now used in the nibs of so-called fiber tipped pens may be used and such materials can be shaped or extruded in a variety of lengths and cross-sections appropriate in the context of the invention. Preferably the material comprising the porous conjugate structure is chosen such that the porous material can be saturated with aqueous liquid within a matter of seconds. Preferably the material remains robust when moist.

In other embodiments, the conjugate structure is a finish or glaze on which is deposited a layer of the detection reagent. In one embodiment, a portion of the membrane carries the conjugate structure. One of skill in the art will appreciate that, in practice, the finish/glaze may not form a true surface layer and the finishing/glazing material may penetrate the thickness of the membrane to some extent. The deposited detection reagent also may penetrate the membrane. According to such embodiments, an aqueous sample can flow along the length of the membrane and in so doing, dissolve the finish/glaze and mobilize the detection reagent, and carry the detection reagent along the membrane.

Detection Reagent

In preferred embodiments, the detection reagent is a detector antibody labeled with a reporter moiety.

In one embodiment, the detector antibody is an antibody, or antigen-binding fragment thereof, that is specific for the Z-AAT protein. The antibody, in various embodiments, exhibits substantially little or no cross-reactivity to PiMM sera or purified wild type AAT.

In another embodiment, the detector antibody is monoclonal antibody LG96, MG97, or an antigen-binding fragment thereof.

In other embodiments, the detector antibody is monoclonal antibody MG97, wherein the capture antibody is monoclonal antibody LG96. In some embodiments, the detector antibody is monoclonal antibody LG96, wherein the capture antibody is monoclonal antibody MG97. In some embodiments, the capture antibody is monoclonal antibody LG96 and the detector antibody is monoclonal antibody LG96.

The reporter moiety can be any of a wide range of materials/reporter systems known in the art. In some embodiments, the reporter moiety comprises a first member of a ligand-receptor pair including, but not limited to, an enzyme (e.g., horseradish peroxidase (HRP), alkaline phosphatase, luciferase, β-galactosidase, glucose oxidase, lysozyme, malate dehydrogenase, glucose-6-phosphate dehydrogenase); metal sol, selenium sol, carbon sol, and the like; colored or colorable particles (e.g., colored or colorable latex particles); colloidal metal particles (e.g., colloidal gold, colloidal silver, colloidal platinum, colloidal selenium). Examples of methods known in the art for detecting the reporter include, but are not limited to, detection methods by visible inspection, ultraviolet (UV) and visible spectrophotometry, fluorimetry and radiation counters.

The reporter moiety may be covalently or non-covalently bound/coupled to the detector antibody. The binding/coupling can be accomplished by any method known in the art. For example, reagents used for binding/coupling include, but are not limited to, glutaraldehyde, p-toluene diisocyanate, various carbodiimide reagents, p-benzoquinone m-periodate, N,Ni-o-phenylenedimaleimide, recombinant methods, and the like.

Blood Separation System

In other embodiments, the device further comprises a blood separation system for receiving the sample, wherein the blood separation system is fluidly coupled to the conjugate structure. In one embodiment, the blood separation system is a blood separation system that partially overlays the conjugate pad.

In some embodiments, the sample does not have to be applied directly to the conjugate structure or the membrane section of the device. In a preferred embodiment, the sample is applied to the blood separation system {e.g., absorptive material/pad) that is fluidly coupled to the conjugate structure. For example, the blood separation system can function as a filter, e.g. to remove blood cells from the sample. Filtered sample can then reach the conjugate structure. In other embodiments, during the course of the filtration process, the addition of reagents can be effected at the same time by dissolving the latter out of components present in the blood separation system in a dry state. Interfering factors can be eliminated from the solution by such components. Thus, for example, the ascorbic acid present in a sample, which might interfere in the use of oxidases and peroxidases as labeling agents, can be rendered ineffective by a suitable oxidizing agent. The blood separation system also can function as an adsorbent that removes interfering factors from the sample by adsorption.

Distal Structure

Preferably, the detection reagent (e.g., labeled antibody) migrates with the liquid sample to the test zone. The flow of sample continues beyond the test zone and sufficient sample is applied to the membrane in order that this may occur. In some embodiments, the device further comprises a distal structure fluidly coupled to the membrane at a distal end of the membrane, wherein the distal structure is configured to provide sufficient flow-through from the proximal end to the distal end. The distal structure at least functions as an absorbent "sink" at the distal end of the membrane. The absorbent sink may comprise, for example, Whatman 3MM chromatography paper.

In one embodiment, the distal structure is an adsorbent pad that partially overlays the membrane at the distal end, wherein the adsorbent pad is configured to provide sufficient flow-through from the proximal to the distal end of the membrane by capillary action.

Methods

In some embodiments, in operation, an aqueous sample is applied to the blood separation system at the proximal end of the device. The sample flows by capillary action through the conjugate structure and conveys the detection reagent from the conjugate structure to the test zone(s), then to the control zone to give rise, for example, to a color signal visible by the naked eye irrespective of whether or not the sample contains the analyte to be determined. The determination of the analyte takes place at the test zone(s). In some embodiments, the user of the device can determine whether the analyte is present in the sample by comparing the signal produced in the two zones.

For example, in one embodiment, if the test is used to determine the presence of a Z-AAT protein in a sample of blood obtained from a mammal, the membrane component of the device can comprise a single test zone having immobilized thereonto monoclonal antibody LG96; and a single control zone having immobilized thereto anti-mouse IgG. A conjugate pad can be overlaid with the membrane at the proximal end of the membrane, wherein the conjugate pad comprises monoclonal antibody MG97 labeled with a reporter moiety such as, for example, colored latex particles. Detection of a visible band at the test zone indicates the presence of the Z-AAT protein in the blood; and detection of a visible band at the control zone confirms that the sample has permeated the membrane sufficiently.

In other aspects, the present invention provides a method for determining a PiZ gene carrier. The method comprises:
(a) subjecting a sample to immunochromatography using an immunochromatographic device comprising a membrane having a capture antibody bound thereto at a test zone, wherein the capture antibody is capable of binding with an analyte, wherein the analyte is a Z-AAT protein present in a sample from a PiZ gene carrier, wherein the capture antibody is monoclonal antibody LG96 or MG97; and
(b) determining a signal at the test zone, wherein the presence of a signal at the test zone indicates that the subject is a PiZ carrier.

In one embodiment, the detection reagent is monoclonal antibody LG96 or MG97, wherein the antibody is labeled with a reporter moiety.

In other embodiments, the PiZ carrier has a phenotype that is any allelic combination having a PiZ allele.

In some embodiments, the phenotype is PiZZ, PiMZ, PiSZ, or PiZ/Null.

In another embodiment, the subject's blood circulation has a Z-AAT protein concentration that is detectable and thereby indicative of the existence of the PiZ allele.

In other embodiments, the PiZ carrier is a heterozygous MZ carrier having an AAT serum level of at least about 80 mg/dl.

In still further aspects, the present invention provides a method for diagnosing a condition or disease associated with AAT deficiency, the method comprising:
(a) subjecting a sample to immunochromatography using an immunochromatographic device comprising a membrane having a capture antibody bound thereto at a test zone, wherein the capture antibody is capable of binding with an analyte, wherein the analyte is a Z-AAT protein present in a sample from a PiZ gene carrier, wherein the capture antibody is monoclonal antibody LG96 or MG97; and
(b) determining a signal at the test zone, wherein the presence of a signal at the test zone indicates that the subject has the condition or disease.

Devices

In other aspects, the present invention provides a device for performing specific binding assays, in particular immunochromatographic assays. Devices can be readily adapted to employ the antibodies and methods of the present invention for detecting Z-AAT. Solid-phase assay devices include, but are not limited to immunochromatographic immunoassay devices, flow-through assay devices, microtiter plates, dipsticks and immunocapillary.

In a preferred embodiment, a device, which can be adapted for use with the antibodies and methods of the present invention, is described by WO 2010/089102, which is herein incorporated by reference for its teaching of a device for liquids of a human or animal body.

In some embodiments, the device is a single use, closed system having a lancet component and a blood collection component via an integrated interface for capillary direct determination of an alpha-1-antitrypsin deficiency.

Figure 16:
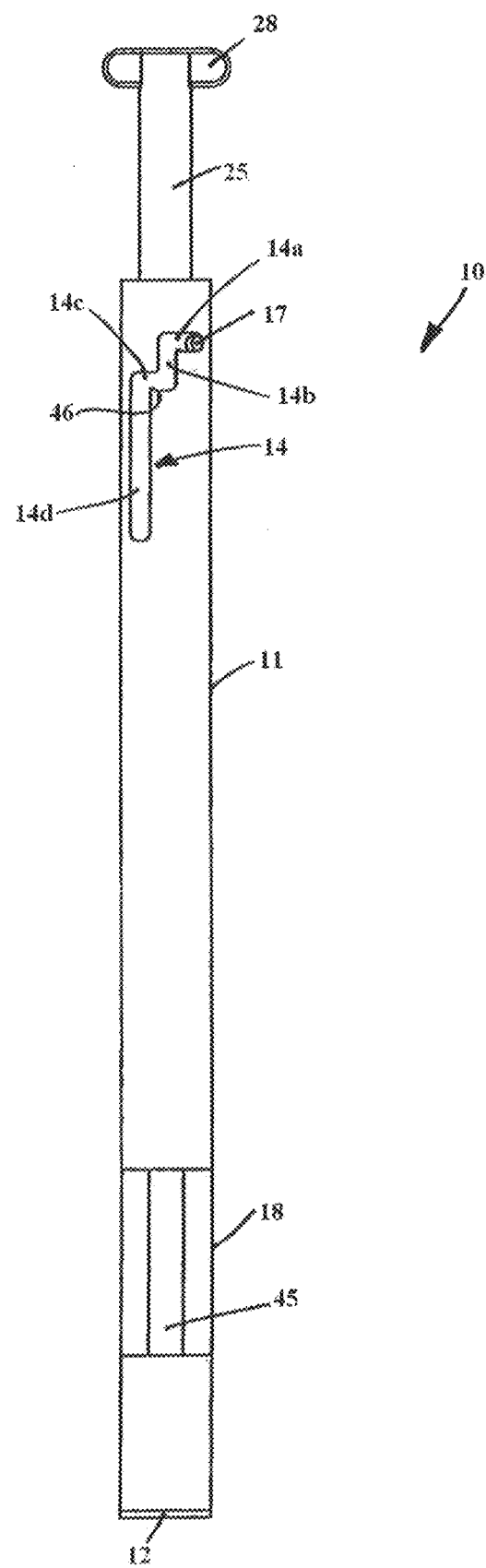
FIG. 16 shows a side view of one embodiment of a device of the present invention.

In one embodiment, the device is configured for performing a sandwich immunoassay for Z-AAT antigen in accordance with immunochromatographic methods and antibodies of the present invention. The embodiment of a device 10, as illustrated in FIG. 16 by way of example, has an elongated, tubular housing 11.

Figure 17:
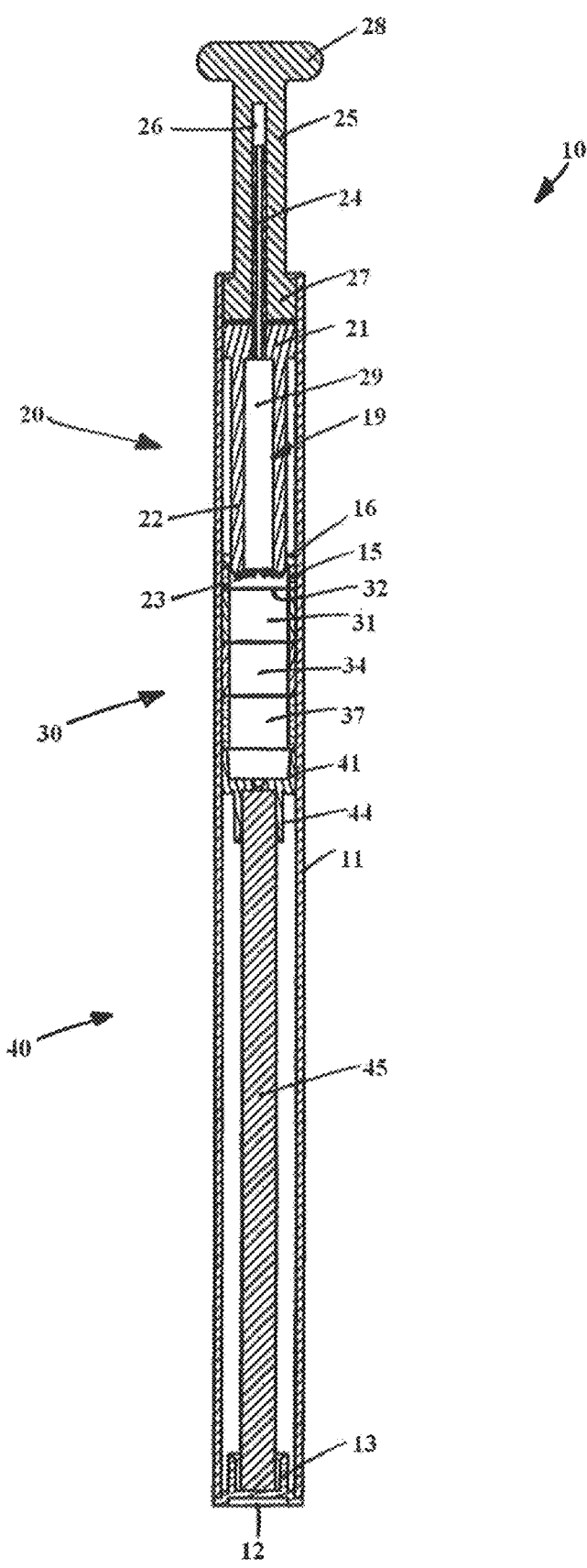
FIG. 17 is a longitudinal section of the device shown in FIG. 16.
Figure 18:
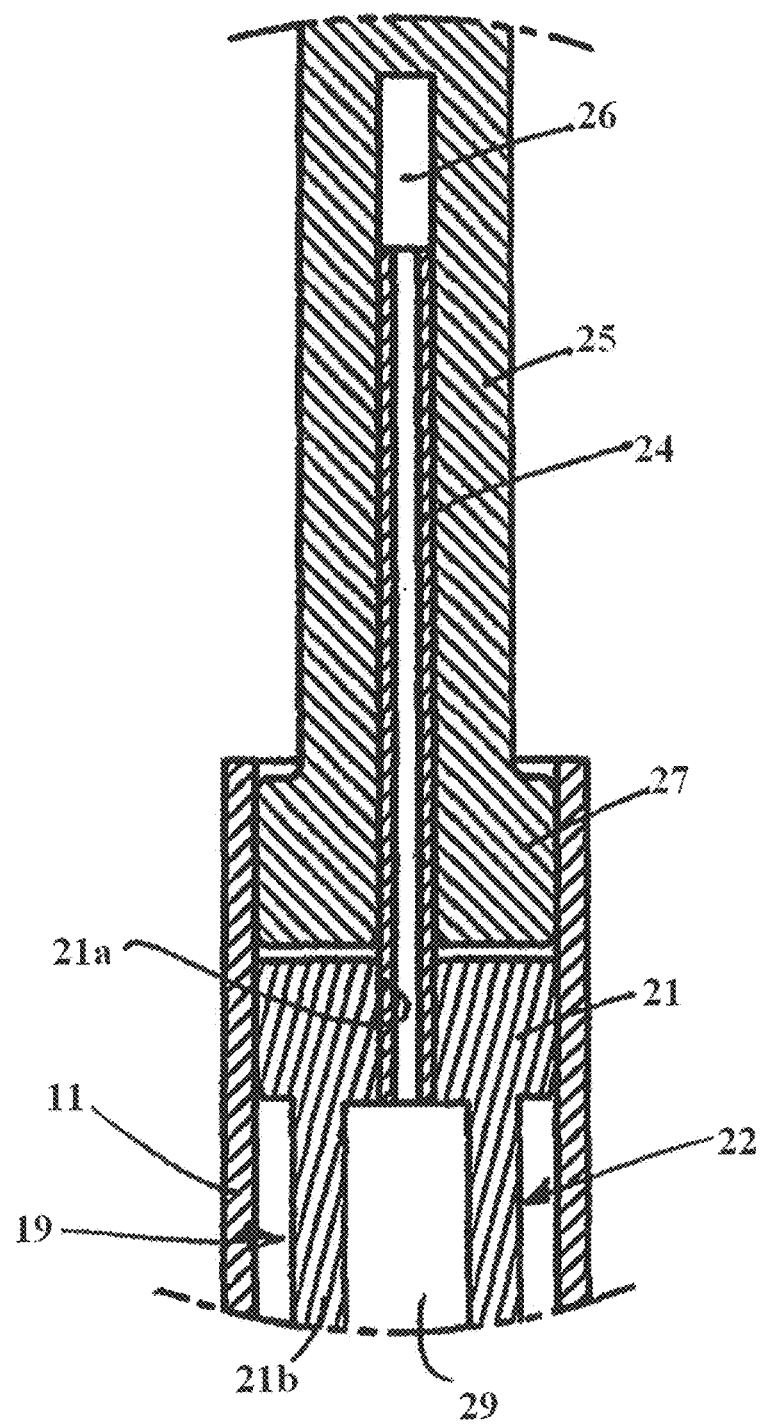
FIG. 18 is an enlarged view of the feeding area of the device shown in FIG. 16.
Figure 19:
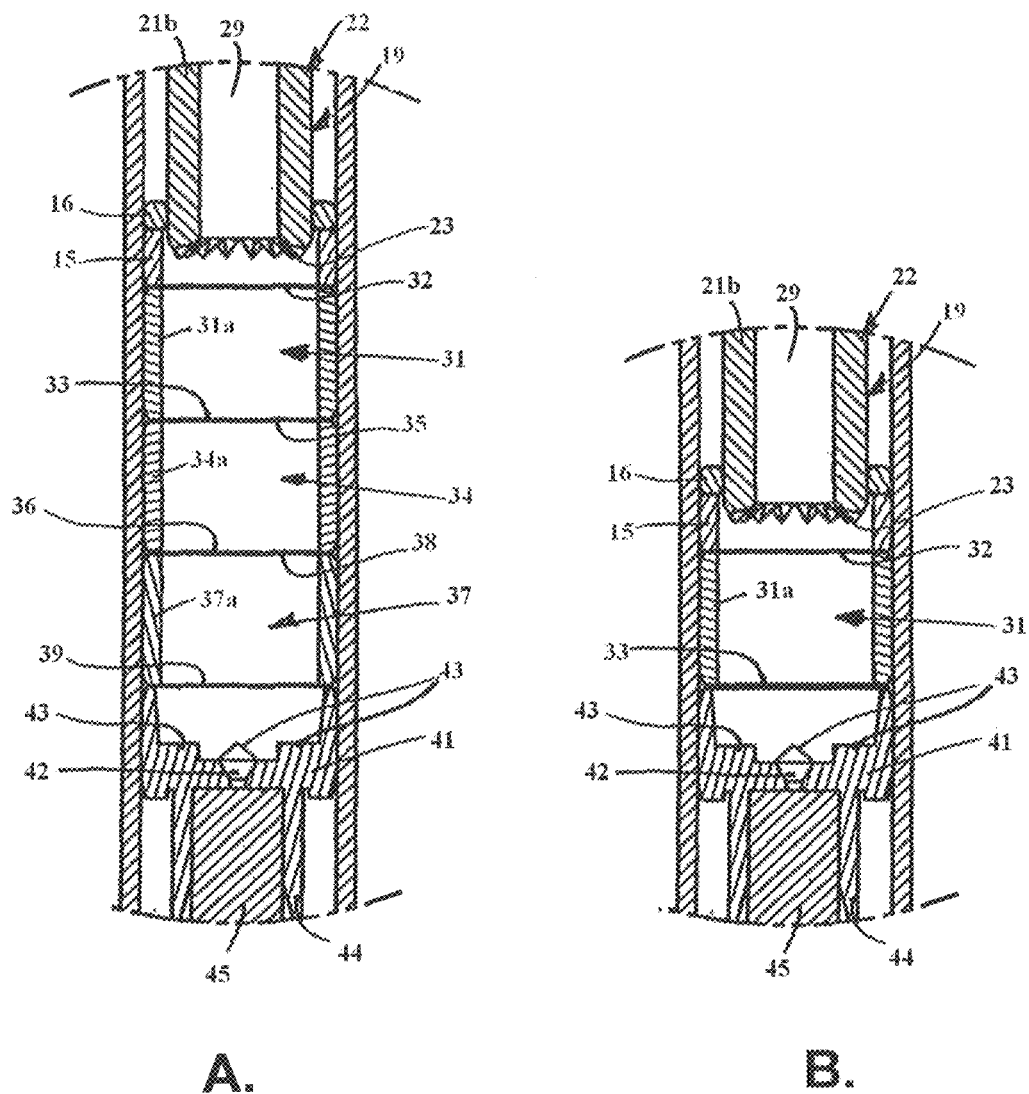
FIG. 19 is an enlarged representation of the reaction area of: (A) the device shown in FIG. 16; and, (B) another embodiment of a device, wherein the device comprises a single cartridge.

A cap 12 is on the inside of the housing 11 facing one side of a holder 13 that holds a strip-shaped element 45. The strip-shaped element 45 extends axially in the housing 11 and is seated, at its proximal end, in a nozzle-shaped intake tube 44 of a cup-shaped separator element 41. The separating element 41, which separates indication area 40 from reaction area 30, has a cup-shaped, upwardly opening cross-section and sits sealingly under a tight fit hi housing 11. Through-hole 42 at the bottom of separating element 41 opens directly on the face of the strip-shaped element 45. Separation element 41 is surrounded by the through-hole 42 of spacers 43 (FIGS. 17 & 19).

In some embodiments, the strip-shaped element 45 comprises a membrane (e.g., a piece of microporous absorbent material such as nitrocellulose), optionally which may be laminated to a backing (e.g., a plastic backing), in contact with the membrane is: (a) a conjugate structure having a detection reagent, such as a detector antibody labeled with a reporter moiety; and (b) a distal structure, e.g. a strip of a second absorbent material (e.g., Whatman 3MM chromatography paper, glass fiber), said distal structure in fluid communication with the membrane in order to assist in pulling the assay fluids through the membrane from its proximal end to the distal end. The distal structure also functions as an absorbent that absorbs the fluids that pass through the membrane.

The membrane comprises a test zone having a capture antibody of the invention immobilized thereon. In one embodiment, the membrane further comprises a control zone to provide a determination that the device has worked. Preferably, the control zone is located downstream from the test zone(s) at which the desired test result is determined. A positive control indicator therefore provides information that the sample at least has permeated the required distance through the membrane. For example, the control zone can be loaded with an antibody or other molecule/reagent that will bind to a detection reagent to confirm that the sample has. sufficiently permeated the membrane. For example, where the detection reagent is a labeled antibody derived from a murine hybridoma, the control zone can comprise anti-mouse IgG. In one embodiment, the capture antibody at the test zone is LG96 and/or MG97; the detection reagent is LG69 that is labeled with a detectable label; and the control zone comprises anti-mouse IgG immobilized thereon. In another embodiment, the capture antibody at the test zone is LG96 and/or MG97; the detection reagent is MG97 that is labeled with a detectable label; and the control zone comprises anti-mouse IgG immobilized thereon.

In some embodiments, one or more cartridges are arranged immediately above the separating element 41 in the axial direction of the housing 11. In the embodiment depicted in FIG. 19A, the device is shown as comprising three cartridges 31, 34, and 37 in the reaction area 30; and in the embodiment depicted in FIG. 19B, a single cartridge 37 device is shown.

By way of example with reference to FIG. 19 A, in one embodiment, each cartridge 31, 34, 37 has a tubular housing part 31a, 34a, 37a whose outer dimensions meet the inner dimensions of the housing 11, and is sealed at the top and bottom by sealing films 32/33 and 35/36 and 38/39. The cartridge(s) may comprise a buffer, reagent, or other chemical substance that is required for the assay. The cartridge(s) may be prefabricated and used in the filled and sealed state under a tight fit in the housing 11 such that the tubular housing portions lie axially on one another. In the embodiment shown in FIG. 19 A, the region of the strip-shaped element 45 facing the cartridge 37 rests with its lower end on the upper edge of the separating member 41. At the opposite upper end of cartridge 31 is a clamping element 15 arranged in the form of a clamping sleeve, which may be clamped under elastic deformation against the inner wall of the housing 11 such that the one or more cartridges are securely positioned and/or held against each other.

A cutting device 19 is arranged above the cartridges 31, 34 and 37, said cutting device comprising a cutting part 22. The cutting part 22 comprises retaining body 21 and tubular extension 21b, which comprises at its bottom end facing the cartridge(s) 31, 34, 37 a cutting knife 23, e.g., a knife comprising cutting teeth. Arranged near the lower end of the tubular projection 21b is an annular or cylindrical sealing element 16, which rests on the inside of the housing 11 and the exterior of the tubular projection 21b and is supported axially on top of the clamping sleeve 15.

Retaining body 21 of the cutting part 22 has an axial center hole 21a in which a capillary tube 24 is inserted. A tubular cap 25 has an internal blind bore 26 in which the protruding top section of the capillary tube 24 is seated. At the upper end of the cap 25 is a handle portion 28, which a user can twist and move cap 25 axially. At the lower end, opposite the handle portion 28 of cap 25 is guide member 27.

Figure 20:
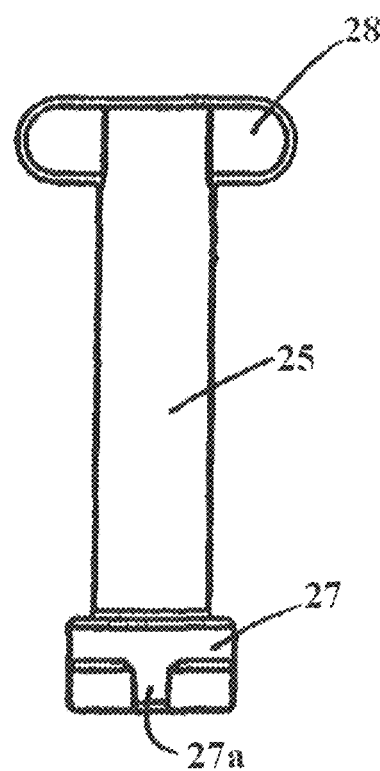
FIG. 20 shows a side view of the cap and the cutting portion of the device shown in FIG. 16.
Figure 20:
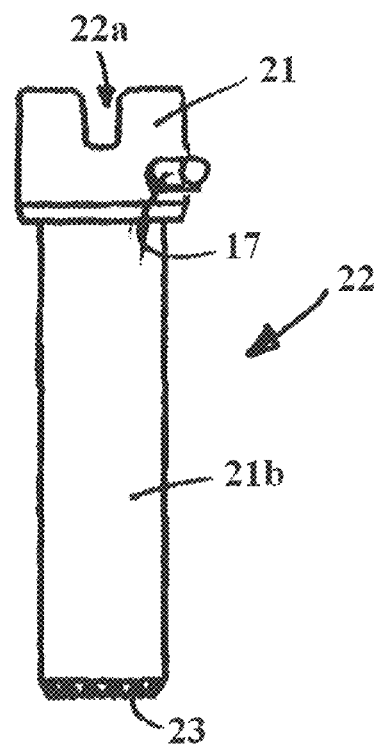

As shown in FIG. 20 shows, holder body 21 of cutting part 22 has a radially outwardly extending guide pin 17 that engages a cam formed in the housing 11 in the form of a slot-shaped gate 14 (see also FIG. 16). With reference to FIG. 16, gate 14 has a first section 14a in the circumferential direction of housing 11 extending first section 14a, a second section 14b in a longitudinal direction of housing 11 extending second section 14b, a third section 14c in the circumferential direction of housing 11 extending third section 14c, and a fourth section 14d in the longitudinal direction of housing 11 extending fourth section 14d. In some embodiments, a slight narrowing cross section may be provided at nose 46 in the transition area between the third section 14c and the fourth section 14d in order to prevent erroneous transfer of the guide pin 17 from section 14c into section 14d. The engagement of the guide pin 17 in gate 14 results in movement of the cutting part 22 relative to housing 11 and covers sections 14a and 14c in the rotations, and sections 14b and 14d in the axial motions.

To perform an assay with the device 10, the sample (e.g., whole blood) to be examined is introduced in the upper region 20. For example, the cap 25 is removed to expose a portion of capillary tube 24, which is then contacted with a drop of blood, for example on the fingertip of a subject. The sample enters into capillary tube 24 by capillary action. Subsequently, the cap 25 is placed with its blind hole 26 on the capillary tube 24 and slid completely such that the volume is reduced between the bottom of the blind bore 26 and the upper end of the capillary tube 24, which leads to an increase in pressure that causes the sample to exit the lower end of the capillary tube 24 into interior 29 of the tubular projection 21b of the cutting part 22.

By placing the cap 25 back onto the device, segment 27a of guide 27 of cap 25 engages with intake 22a so that a transmission of a rotational movement of cap 25 on the cutting part 22 is performed. The user rotates cap 25, and thereby also cutting part 22 is rotated as far as the guide pin 17 can move in section 14a. Then, the user presses down onto cap 25, thereby also downward on cutting part 22 in the axial direction of the housing 11 as far as the guide pin 17 can move in section 14b— as a result of this axial displacement of cutting part 22, cutting blade 23 comes in contact with the upper sealing film 32 of the cartridge 31 thereby destroying/cutting film 32. Upon destruction of film 32, the sample that is present in interior 29 of tubular projection 21b comes into contact with the content of cartridge 31. The other cartridges 34 and 37 are still closed.

To initiate the next phase of testing, the user rotates cap 25 again, whereby the guide pin 17 is moved along section 14c to the transition area between section 14c and section 14d. In this position, it is possible for the user to push cap 25 further into housing 11 such that cutting portion 23 is moved to a sufficient distance within housing 11 to result in destruction of both the sealing film 33 of cartridge 31 and the sealing film 35 of cartridge 34. In order to also destroy/cut sealing films 36, 38, and 39, cap 25 is further moved to an appropriate distance along section 14d. In this way, the sample successively also comes into contact with the contents of cartridges 34 and 37. The sample then passes into the cup-shaped separator 41 and flows through the through-hole 42 to contact the immediately underlying strip-shaped element 45, where it can cause a color change, which can be visualized through a window 18.

In other embodiments, the device further comprises a lancet 50 at a distal end of housing 11 (see, e.g., FIGS. 21-25). Preferably, the lancet is a detachable lancet.

Figure 21:
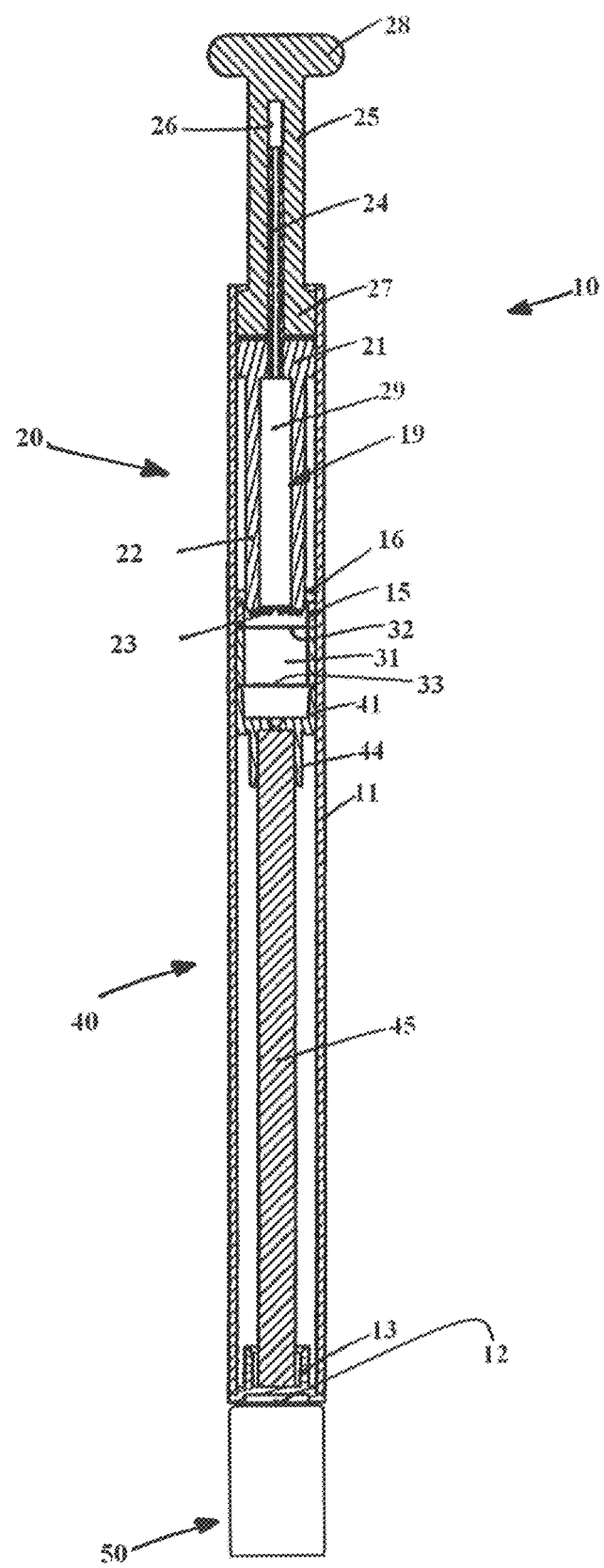
FIG. 21 is a longitudinal section of one embodiment of a device of the present invention.
Figure 22:
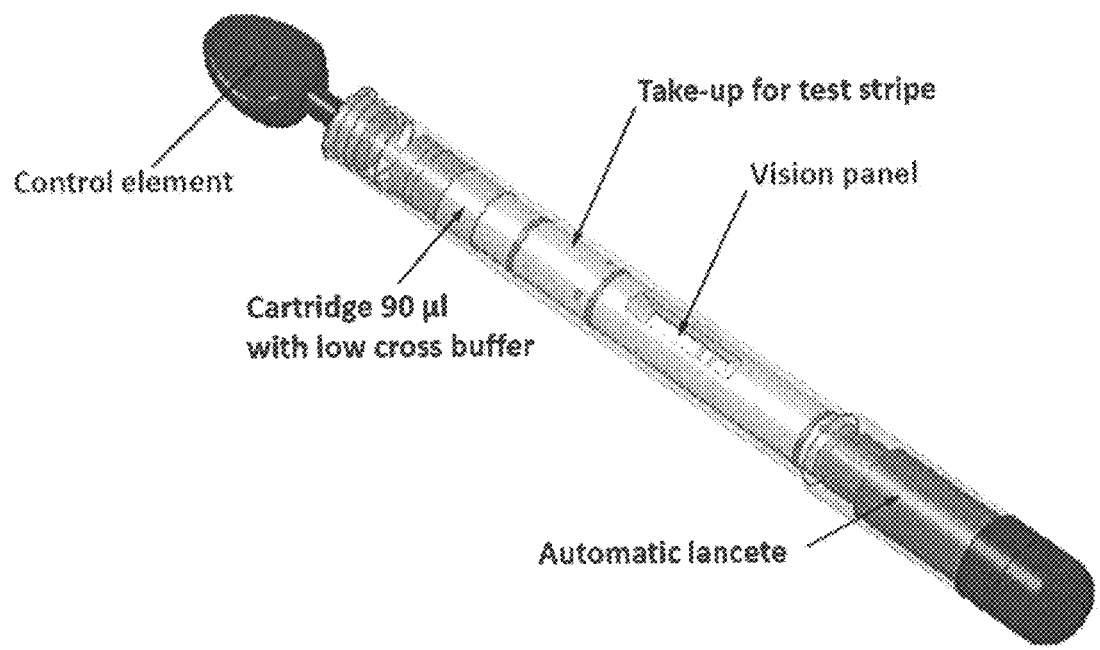
FIG. 22 is another embodiment of a device of the present invention.
Figure 23:
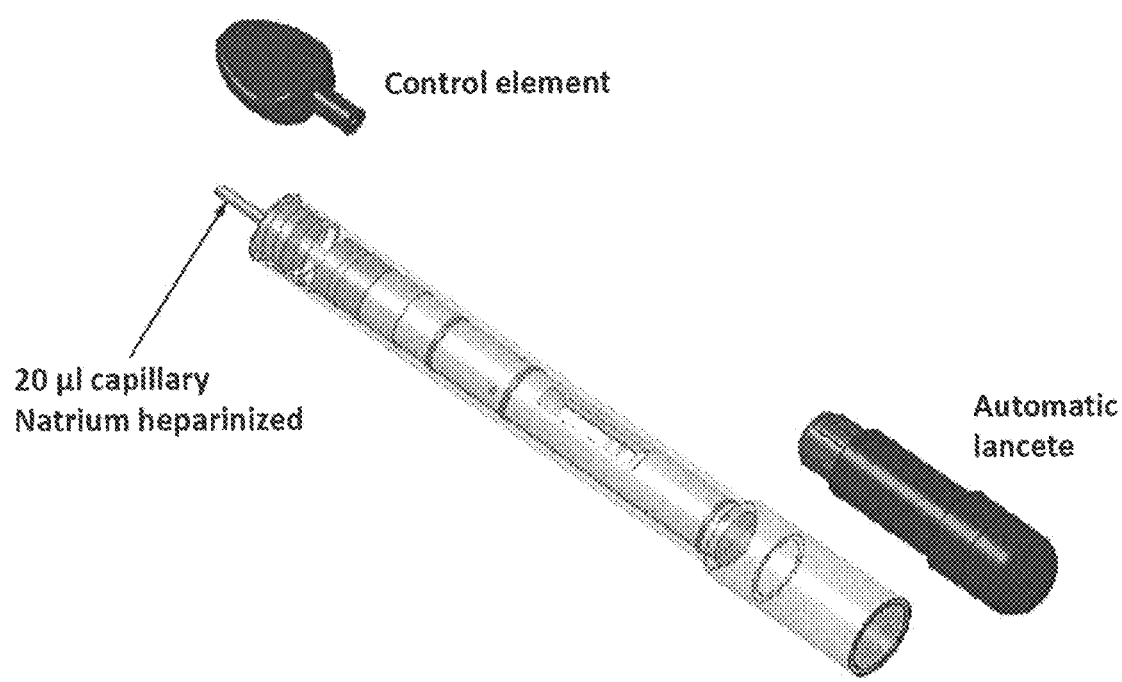
FIG. 23 is a device of the present invention in accordance with some embodiments.
Figure 24:
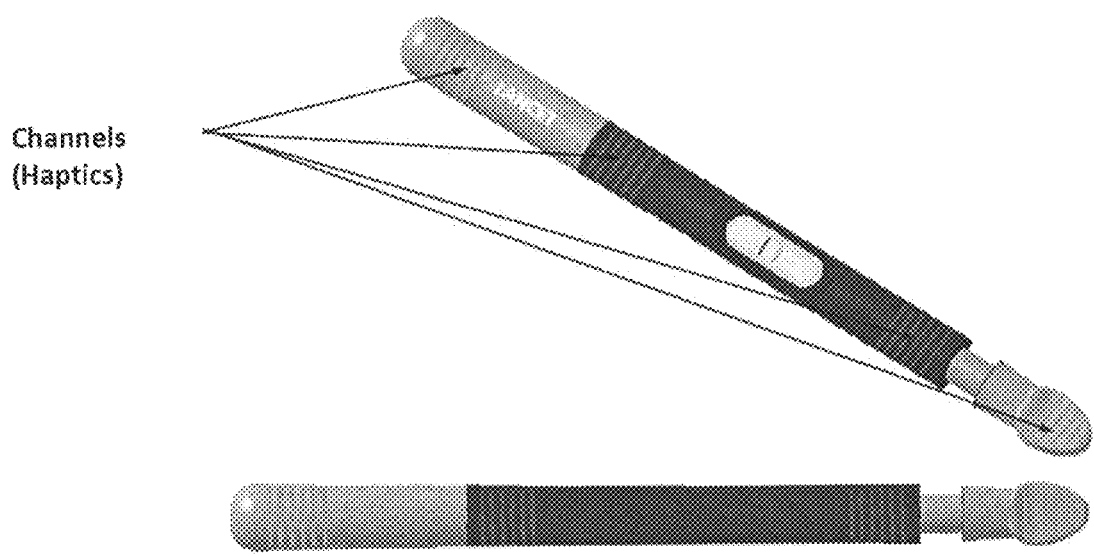
FIG. 24 is a device of the present invention in accordance with other embodiments.
Figure 25:
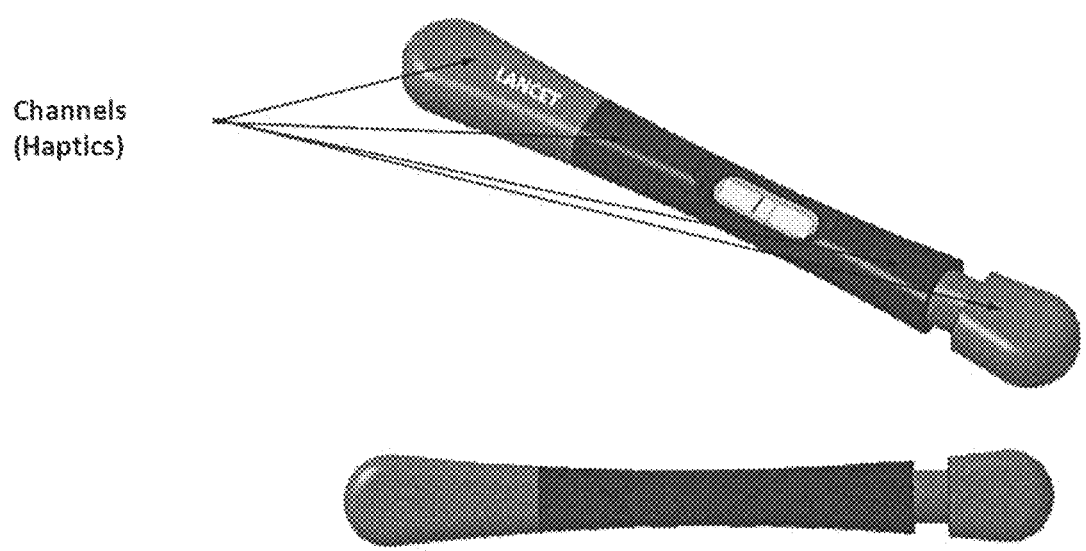
FIG. 25 is a device of the present invention in accordance with still further embodiments.

With reference to FIG. 21, to perform the assay, an opening is formed in a body tissue at a sample site using the lancet component of the device to obtain a sample. The cap 25 is then removed to expose a portion of capillary tube 24, which is then contacted with the sample. The cap 25 is then placed back onto the device 10 with its blind hole 26 on the capillary tube 24 and slid completely such that the volume is reduced between the bottom of the blind bore 26 and the upper end of the capillary tube 24. In one embodiment, a sealing film 32 of cartridge 31 is destroyed whereby the sample is allowed to contact the buffer contained within cartridge 31 to form a sample/buffer composition. Then, upon destruction of sealing film 33, the sample/buffer composition contacts the strip-shaped element 45, which in some embodiments, comprises a membrane; a conjugate structure having a detection reagent, wherein the detection reagent is a detector antibody labeled with a reporter moiety; and a distal structure in fluid communication with the membrane, wherein the sample/buffer composition contacts the conjugate structure such that the sample/buffer composition is drawn up into it by capillarity (wicking), thus bringing the sample/buffer composition into contact with the detection reagent. The sample/buffer/detection reagent mixture is continuously drawn up into the membrane portion of the strip-shaped element 45 whereby the mixture contacts the capture antibody immobilized onto the membrane at the test zone thereby allowing any Z-AAT antigen which may be present in the mixture to bind to the capture antibody. Optionally, a wash solution may be wicked into the device after a sufficient amount of time after the mixture is contacted with the capture antibody. The detectable label of the detector antibody is then visualized in the area of immobilized capture antibody. In a preferred embodiment of the assay device, a positive control is included on the membrane in the vicinity of, but distinct from, the immobilized capture antibody, preferably immobilized on the membrane in an area contacted by the migrating sample fluid after it contacts the area of immobilized capture antibody.

In some aspects, the present invention provides an immunoassay device comprising: a membrane having a Z-AAT protein capture area defined by a capture antibody immobilized thereto, wherein the capture antibody is an anti-Z-AAT protein antibody.

In one embodiment, the capture antibody is LG96 or fragment thereof.

In another embodiment, the capture antibody is MG97 or fragment thereof.

In some embodiment, the device further comprises a sample application area and a flow path from the sample application area to the Z-AAT protein capture area, wherein the presence or amount of a Z-AAT protein in a fluid sample can be determined by formation of a complex between the capture antibody and the Z-AAT protein that may be present in the fluid sample.

In other embodiments, the device further comprises a conjugate structure located in the flow path, wherein the conjugate structure comprises a detection reagent specific for the Z-AAT protein, the detection reagent being mobile or mobilizable.

In one embodiment, the detection reagent is a detector antibody.

In some embodiments, the detector antibody is LG96 or fragment thereof.

In other embodiments, the detector antibody is MG97 or fragment thereof.

In another embodiment, the detector antibody is labeled with a reporter moiety.

In other embodiments, the detector antibody is a gold-conjugated detector antibody.

In still further embodiments, a source of the fluid sample is capillary blood, serum, or plasma.

In other aspects, the present invention provides an immunoassay device for determining the presence or amount of a Z-AAT protein in a fluid sample. The device comprises:
a sample application area;
a microporous membrane having a Z-AAT protein capture area defined by a capture antibody immobilized thereto, wherein the capture antibody is LG96 or antigen-binding fragment thereof;
a flow path from the sample application area to the Z-AAT protein capture area, wherein the presence or amount of a Z-AAT protein in a fluid sample can be determined by formation of a complex between the capture antibody and the Z-AAT protein that may be present in the fluid sample; and
a conjugate structure located in the flow path, wherein the conjugate structure comprises a detection reagent specific for the Z-AAT protein, the detection reagent being mobile or mobilizable, wherein the detection reagent is gold-conjugated LG96 or a gold-conjugated antigen-binding fragment thereof.

In one aspect, a method for detecting a Z-AAT protein in a subject is provided. The method comprises:
applying a biological sample from the subject to the immunoassay device of present invention; and
detecting a complex that is formed between the capture antibody and the Z-AAT protein that may be present in the fluid sample, wherein detection of the complex indicates the presence of the Z-AAT protein in the sample.

Kits

In one aspect, the present invention provides a method for determining a subject's predisposition to developing a condition or disease associated with AAT deficiency, the method comprising:

(a) subjecting a sample to immunochromatography using an immunochromatographic device comprising a membrane having a capture antibody bound thereto at a test zone, wherein the capture antibody is capable of binding with an analyte, wherein the analyte is a Z-AAT protein present in a sample from a PiZ gene carrier, wherein the capture antibody is monoclonal antibody LG96 or MG97; and (b) determining a signal at the test zone, wherein the presence of a signal at the test zone is indicative of the subject's predisposition to developing the condition or disease.

The present invention, in other aspects, provides a kit comprising:
(a) an immunochromatographic device in accordance with the present invention, wherein the capture antibody is monoclonal antibody LG96 or MG97; and
(b) a detection reagent.

In some embodiments, the detection reagent is a detector antibody having a reporter moiety conjugated thereto.

In one embodiment, the detector antibody is monoclonal antibody LG96 or MG97, wherein the antibody is labeled with a reporter moiety.

In another aspect, the present invention provides a kit comprising monoclonal antibody LG96, MG97, or both.

In other aspects, the device and reagents for performing the immunoassay may be packaged in the form of a kit. For example, such a kit may include an appropriate assay device, antibody reagents, and/or reagents for development of the assay such as buffers and/or, if needed, reagents for detection of the chosen label.

In some aspects, the present invention provides a kit for determining the presence of a Z-AAT protein in a biological sample of a subject, said kit comprising a device as described herein, optionally with reagents and/or instructions for use.

In other embodiments, the kit optionally may further include other materials/components desirable from a commercial and user standpoint, including lancets, buffers (e.g., Sample Buffer, CANDOR Bioscience GmbH, Wangen, Germany), diluents, filters, capillaries (e.g., 20 µl capillary), needles, and/or syringes, for example for collecting/obtaining a biological sample.

In still further embodiments, the kit may also include a system enabling detection of the test results. Results may be detected visually or instrumentally depending on the label present on the complexes. In a preferred embodiment, results are visually detected.

EXAMPLES

Example 1

Monoclonal Antibodies

Hybridomas LG96 and MG97 were prepared by immunizing BALB/c mice with polymeric human alpha 1-antitrypsin (AAT) in complete Freud's Adjuvant. The mice were immunized intra-peritoneal; intervals between immunizations were 7-8 days. Immunized mice spleen cells were fused with the plasmacytoma cell line NSW. Hybridoma supernatants were screened for the presence of monoclonal antibodies by ELISA using microtiter plates coated with polymeric hAAT or serum from AAT deficiency PiZZ patients.

Selected hybridomas were cloned and screened again to select those which produce antibody against polymeric AAT but not native AAT. The monoclonal antibodies of hybridomas LG96 and MG97 appeared to recognize polymeric AAT and specifically react with PiZ serum.

Hybridomas were frozen in specific medium (DMEM with 20% FCS and 10% DMSO) cell concentration in each vial was 2×106 cells/ml. Cells were kept in nitrogen. Cells can be recovered using DMEM-10 medium or 20% serum.

Example 2

Testing of Antibodies LG96 and MG97 Against the PiZZ Type of AAT

Monoclonal antibodies LG96 and MG97 were tested on their ability to bind the native PiZZ type in a sandwich-ELISA. Small amounts of cell culture supernatants comprising the antibodies were obtained and both antibodies were partially purified by CANDOR Bioscience GmbH (Wangen, Germany).

Testing of Matching Pairs, Sandwich-ELISA

All used immunoassaybuffers were provided by CANDOR Bioscience. The microtiterplate (MaxiSorp™, Nunc, Langenselbold, Germany) was coated with partially purified antibodies LG96 or MG97, respectively, by adding 150 µl of the respective capture antibody at 1 µg/ml in Coating Buffer pH 9.6 (Product Number 121) to each well and incubated for 3 h at room temperature under shaking conditions. After removing the coating solution the plates were blocked by adding 300 µl Blocking Solution (Product Number 110) to each well and incubated over night at 4° C. The plate was washed three times with Washing Buffer (Product Number 140). Afterwards, the human sera (pooled genotyped ZZ-serum or MM-serum) were diluted with Sample Buffer (Product Number 105) 1:20 and 1:80 (5% and 1.25% serum) containing 1 µg/ml LG96HRP or MG97HRP respectively. Sample Buffer without serum acted as a negative control (0%). 150 µl of these mixtures were added to each well and incubated for 2 h at room temperature under shaking conditions. After the incubation step, the plate was washed three times. Then 150 µl TMB Solution (Kem-En-Tec, Denmark) was added to each well and incubated for 15 min. The reaction was stopped with addition of 50 µl 2 N $H_2SO4$. Absorbance at 450 nm was determined using a microplate reader.

Testing for Cross-Reactivities

The microtiterplate (MaxiSorp™, Nunc) was coated with purified AAT (M-form, BA672, Acris GmBH, Germany) by adding 150 µ*** of AAT at 1 in Coating Buffer pH 7.4 µg/ml.

(Product Number 120) to each well and incubated for 6 h at room temperature under shaking conditions. After removing the coating solution the plates were blocked by adding 250 µl.

Blocking Solution (Product Number 110) to each well and incubated over night at 4° C. The plate was washed four times with Washing Buffer (Product Number 140). Afterwards the purified, Z-specific antibodies LG96 and MG97 and the commercially available antibodies F43.8.1 (Monosan®, Uden, The Netherlands) and 1AT (Acris Antibodies GmBH, Herferd, Germany), both directed against the M-form, were serial-diluted with Sample Buffer (Product Number 105) to yield different assay concentrations of each antibody (1,000 ng/ml, 100 ng/ml, 10 ng/ml, 5 ng ml, 2.5 ng/ml, 1.25 ng/ml 0.625 ng ml and 0 ng/ml). 150 µl of each serial-diluted antibody were added to the wells and incubated for 2 h at room temperature under shaking conditions. After the incubation step the plate was washed four times. For detection, a HRP-labeled secondary antibody was used (Anti-Mouse-IgG-HRP 610-703-124, Biotrend, Germany), which was diluted with Sample Buffer to 0.5 and added to each well followed by an incubation step about 2 h at room temperature under shaking conditions. Afterwards the plate was washed four times. Then 150 µl TMB Solution (Kem-En-Tec, Denmark) was added to each well and incubated for 26 min. The reaction was stopped with addition of 50 µl 2 N $H_2SO_4$. Absorbance at 450 ran was determined using a microplate reader.

Figure 2:
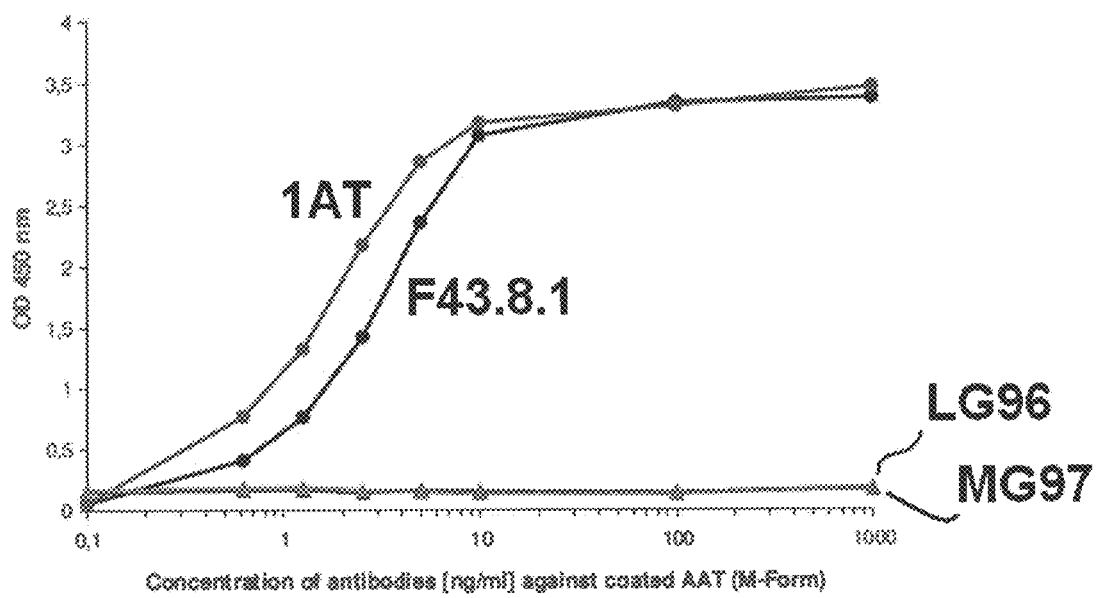
FIG. 2 shows the results of testing for cross-reactivities of monoclonal antibodies LG96, and MG97 with coated AAT (M-form). The M-specific antibodies F43.8.1 and 1AT act as positive controls and both show very strong specific binding to coated AAT (M-form). In contrast antibodies LG96 and MG97 show no binding to coated M-form of AAT.
Figure 3:
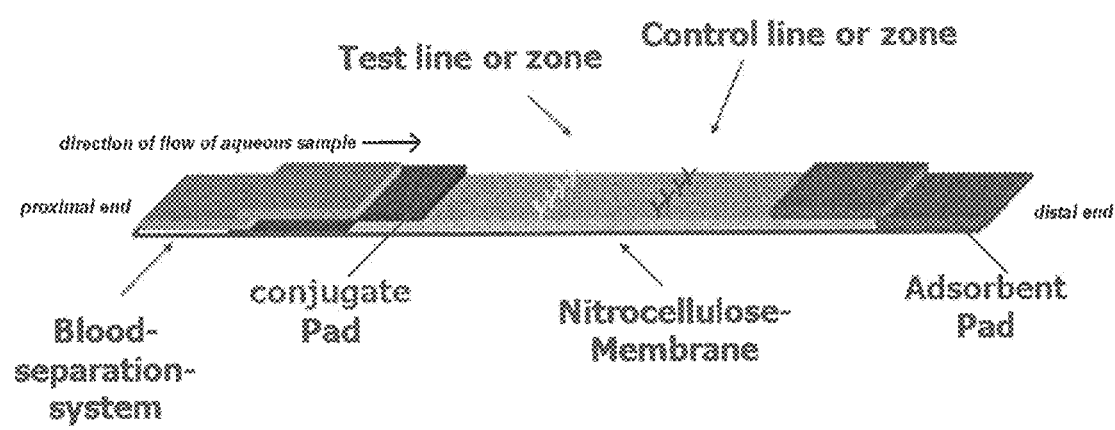
FIG. 3 illustrates a schematic layout of a lateral flow assay (LFA) device for immunochromatography in accordance with one embodiment of the present invention.
Figure 4:
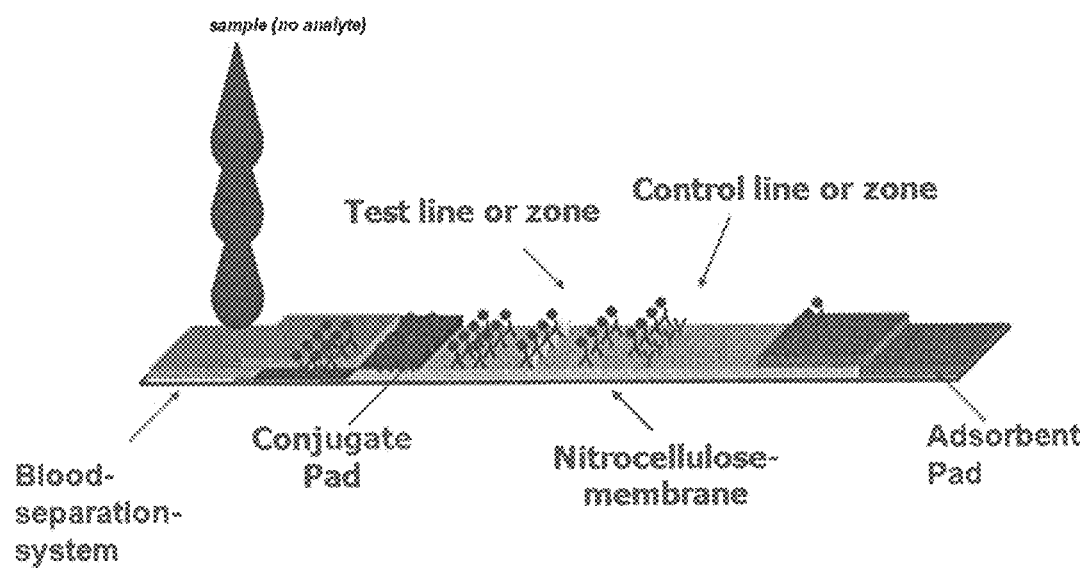
FIG. 4 illustrates a schematic layout as in FIG. 3, wherein the sample does not contain the target analyte.
Figure 5:
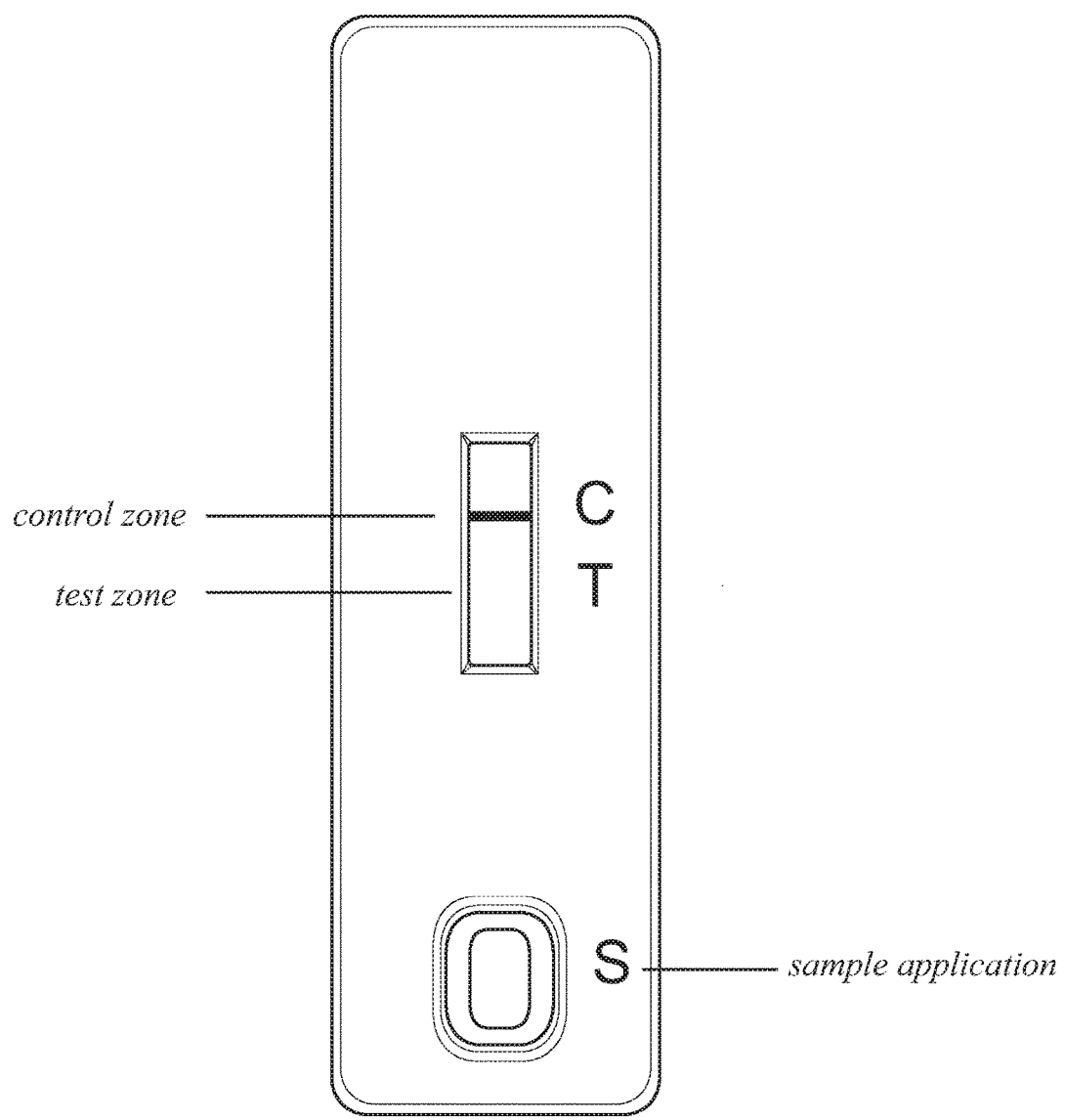
FIG. 5 is a picture of a LFA device, wherein the immunochromatographic components are depicted as encased in a housing made of, for example, a plastic material. The test line or zone is shown as absent thereby indicating that the test results are negative for the presence of the analyte in the sample. The control line or zone is positive indicating that the device worked properly.
Figure 6:
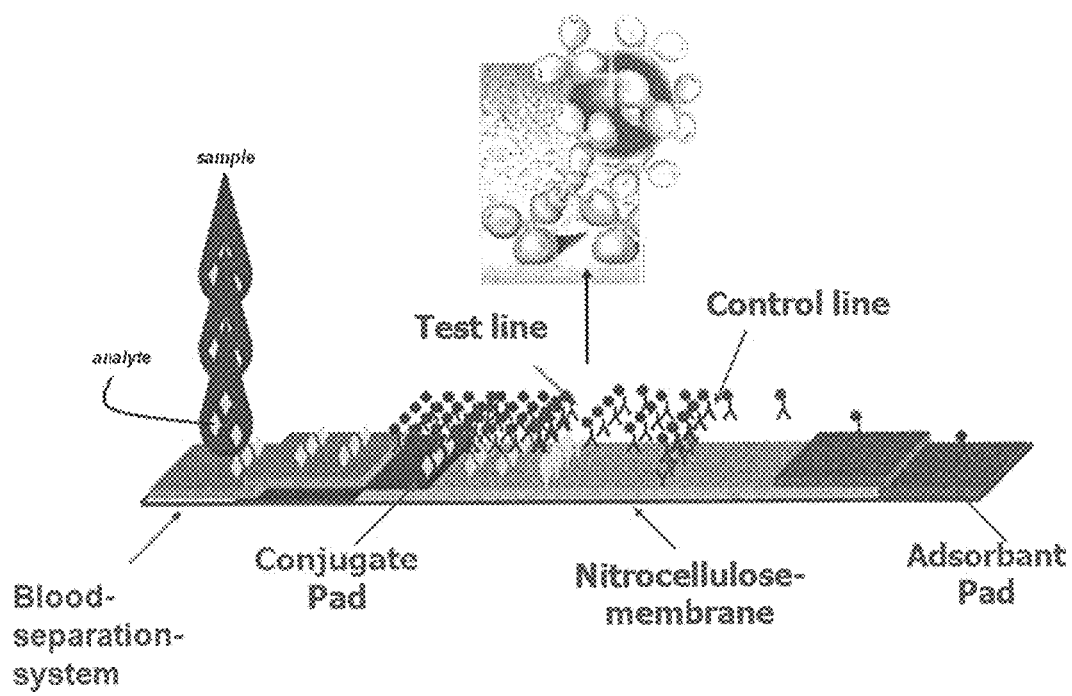
FIG. 6 illustrates a schematic layout as in FIG. 3, wherein the sample contains the target analyte.
Figure 7:
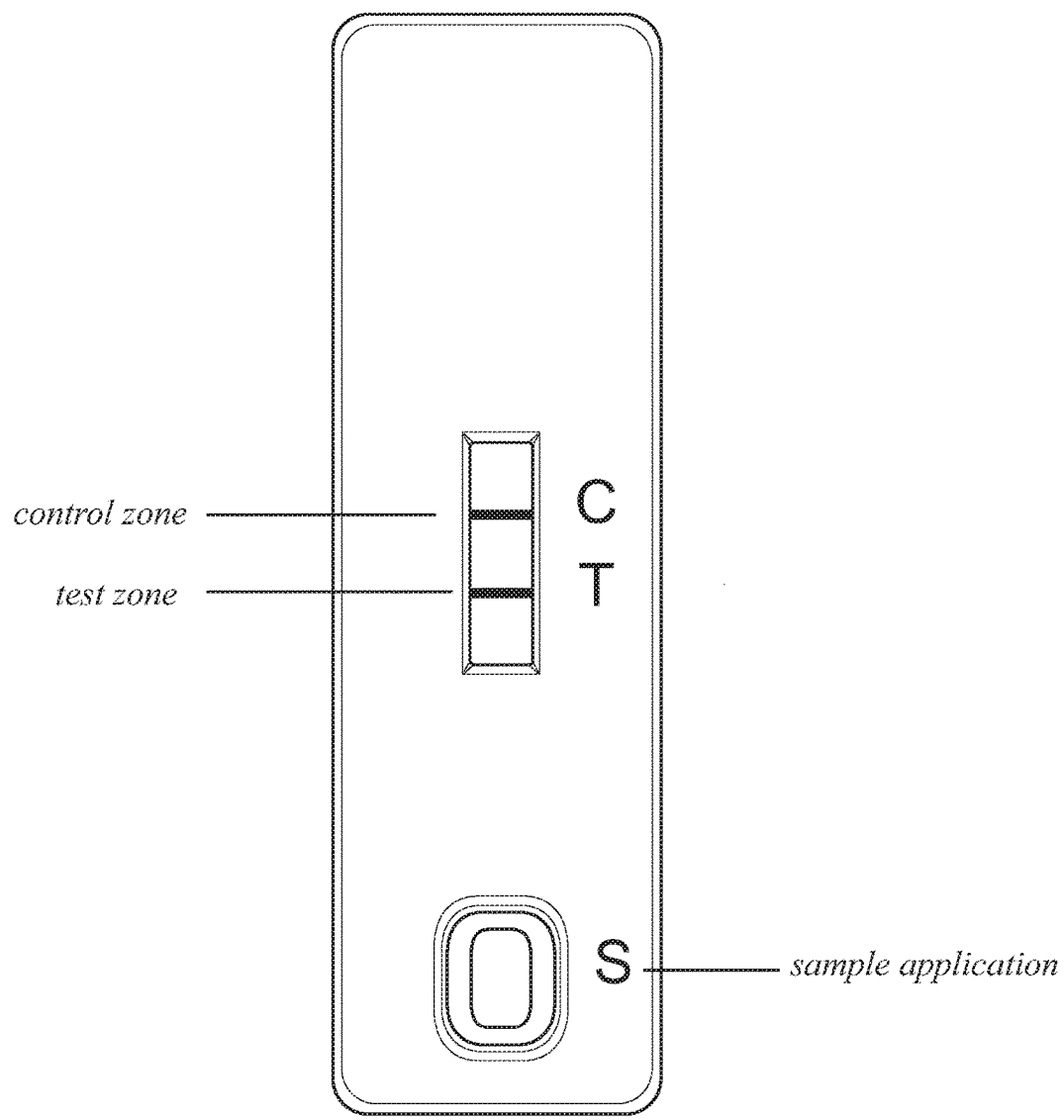
FIG. 7 is a picture of a LFA device, wherein the immunochromatographic components are depicted as encased in a housing as in FIG. 5. The test line or zone is shown as present thereby indicating that the test results are positive for the presence of the analyte in the sample. The control line or zone also is positive indicating that the device worked properly.
Figure 8:
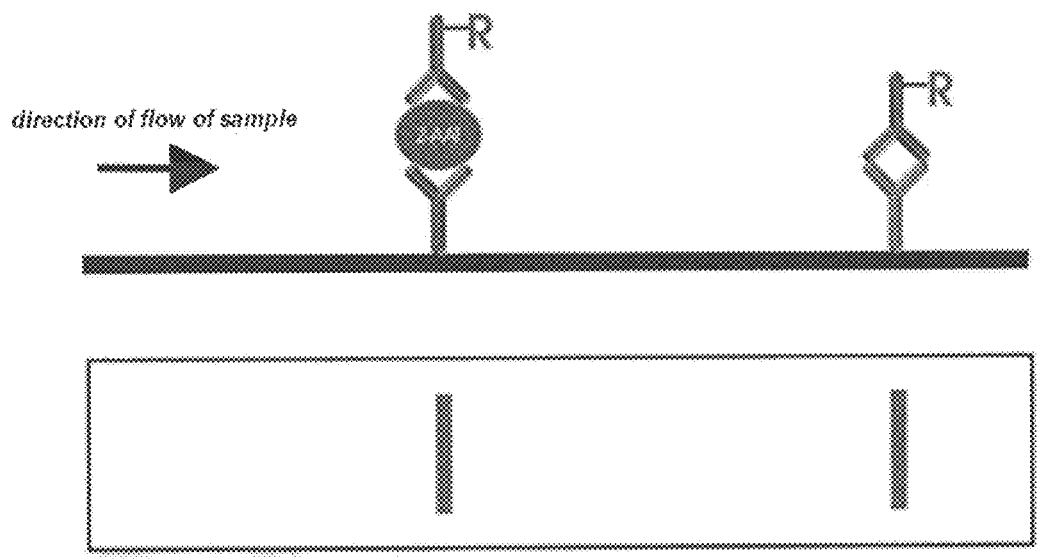
FIG. 8 illustrates the principle of an LFA in accordance with one embodiment of the present invention, wherein the sample is blood from a ZZ-Type individual. Capture antibody LG96; Detector antibody MG97 conjugated with HRP; Control antibody: Ig.
Figure 9:
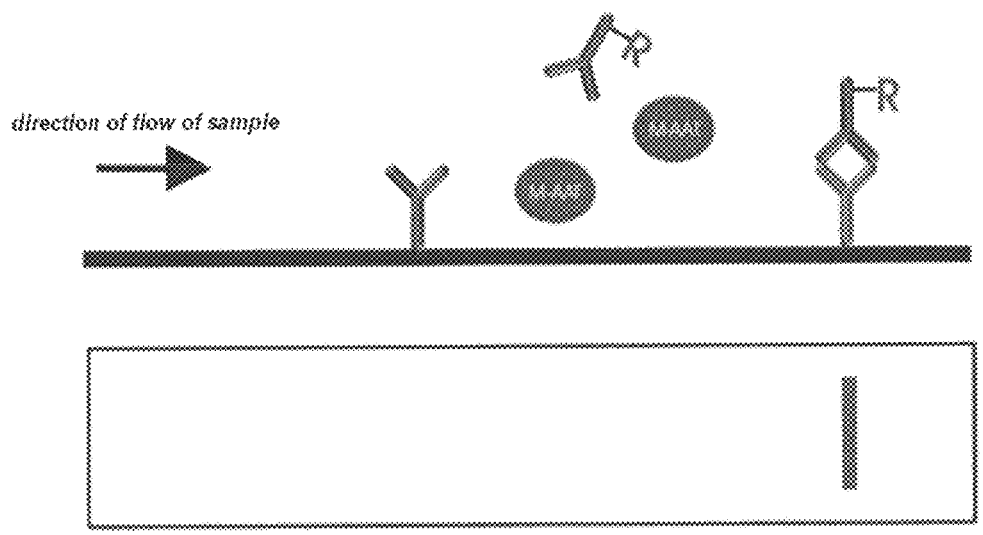
FIG. 9 illustrates the principle of an LFA in accordance with another embodiment of the present invention, wherein the sample is blood from a MM-Type individual. Capture antibody LG96; Detector antibody MG97 conjugated with HRP; Control antibody: Ig.
Figure 10:
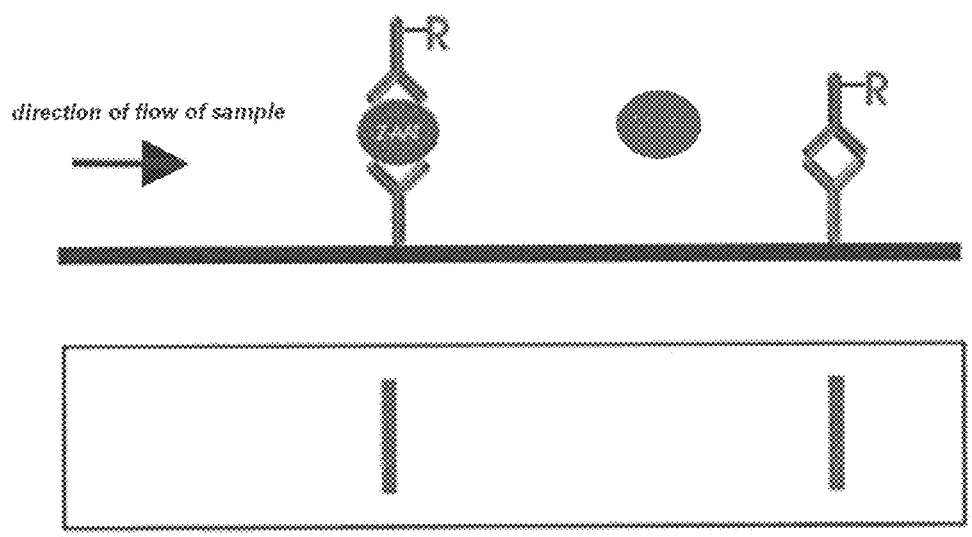
FIG. 10 illustrates the principle of an LFA in accordance with other embodiments of the present invention, wherein the sample is blood from a MZ-Type individual. Capture antibody LG96; Detector antibody MG97 conjugated with FIRP; Control antibody: Ig.
Figure 11:
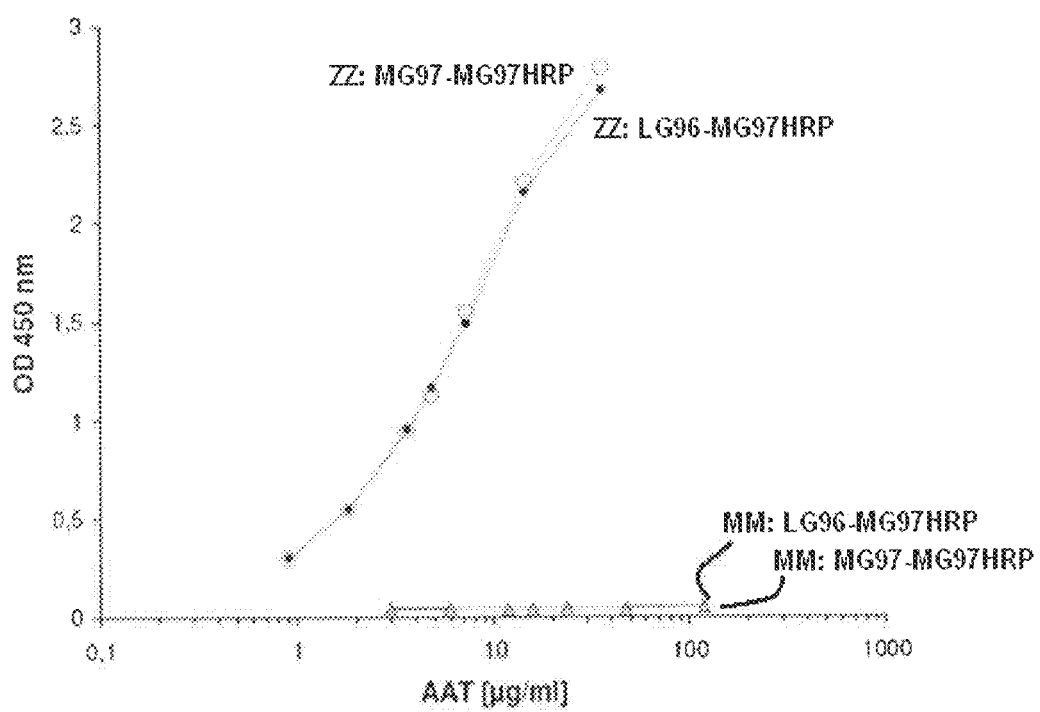
FIG. 11 shows the results of binding curves of LG96-MG97HRP on ZZ- and MM-serum.
Figure 12:
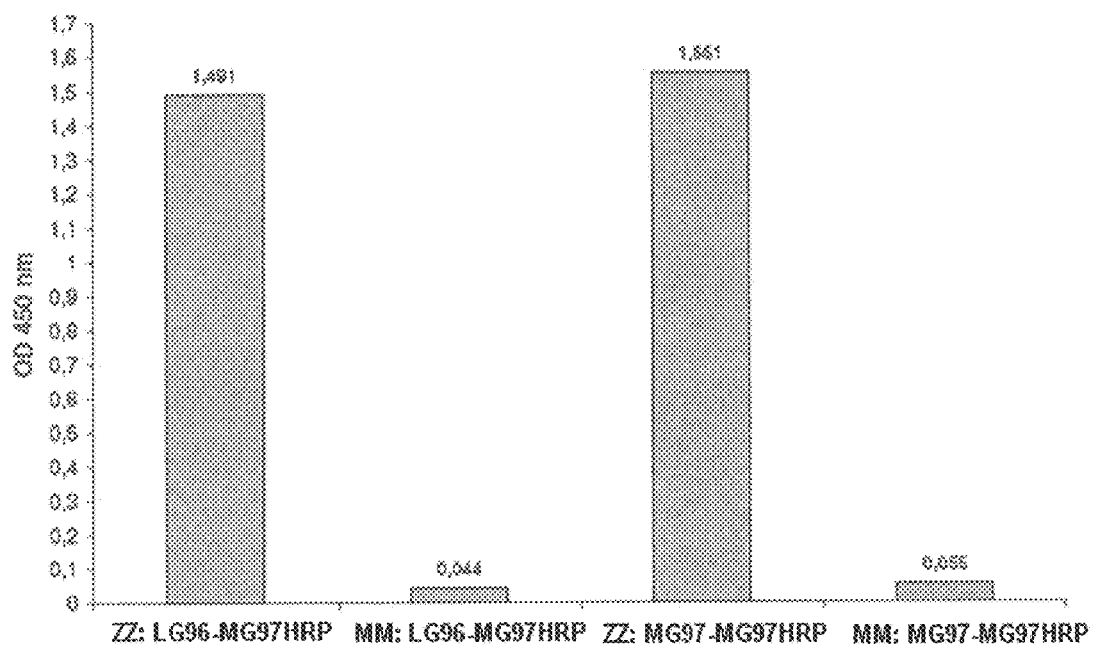
FIG. 12 shows the results of specific binding of LG96-MG97HRP on ZZ-serum. No binding on MM-serum.

The results are shown in FIGS. 1 and 2. FIG. 1 shows a sandwich-ELISA (testing of matching pairs) where both antibodies were used either as capture antibodies or as detector antibodies, the latter labeled with horseradish-peroxidase (HRP). Pooled human sera of 10 patients carrying either the PiZZ- or PiMM-type of AAT (genotyping not shown) were used as antigen solution. Using partially purified antibodies, a positive specific binding to the pooled PiZZ type serum was observed and no cross-reactivity to the pooled PiMM type serum.

The results of an additional test for cross-reactivities are shown in FIG. 2. Here, the purified M-form of AAT was coated on ELISA-wells and the binding of the native antibodies LG96 and MG97 was determined. In contrast to the specific binding of the M-specific control antibodies 1AT and F43.8.1 to coated M-type of AAT, the antibodies LG96 and MG97 show no cross reactivity to the M-type of AAT.

The results show that monoclonal antibodies LG96 and MG97 can be successfully used in a sandwich-ELISA against PiZZ type of AAT. Monoclonal antibodies LG96 and MG97 can be used as assay antibodies in a sandwich-format immunoassay specific for PiZZ type of AAT without cross reactivities to the PiMM type.

Example 3

Development of a Z-AAT Reference ELISA

Figure 13:
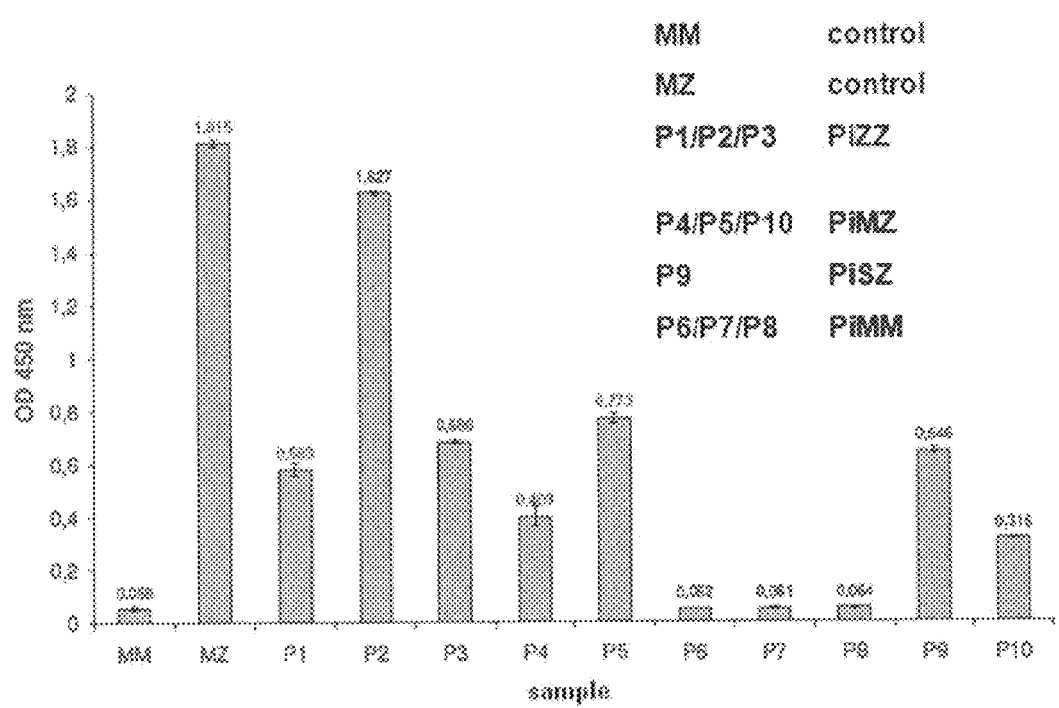
FIG. 13 shows the results of screening of real samples (1:20 diluted) in blank tests.

Ten samples (blank tests) of different subjects (P1-P10) were screened for the existence of Z-AAT with a 100% hit ratio (FIG. 13). All samples with Z were indicated, those without Z (such as MM) not.

Example 4

Additional ELISA Testing

Serum samples from a ZZ-patient (serum #1 and 2), from a MZ-patient being substituted with Prolastin® (serum #3 and 4), and from a control person (MM; serum #5+6) were used. The serum samples 1-6 (described above) were measured. Serum #1 with a known concentration of 36 mg/dl (determined by nephelometry) was used as standard. The concentration of serum samples #2-6 was determined within the ELISA testing (Table 1).

TABLE 1

Z-protein concentration within the serum samples 1-6.

| | Serum #1 (PiZZ) | Serum #2 (PiZZ) | Serum #3 (MZ) | Serum #4 (MZ) | Serum #5 (PiMM) | Serum #6 (PiMM) |
|---|---|---|---|---|---|---|
| Konz. Z-Protein [mg/dL] | 36.0 | 34.0 | 35.8 | 34.1 | 0.0 | 0.0 |

Figure 14:
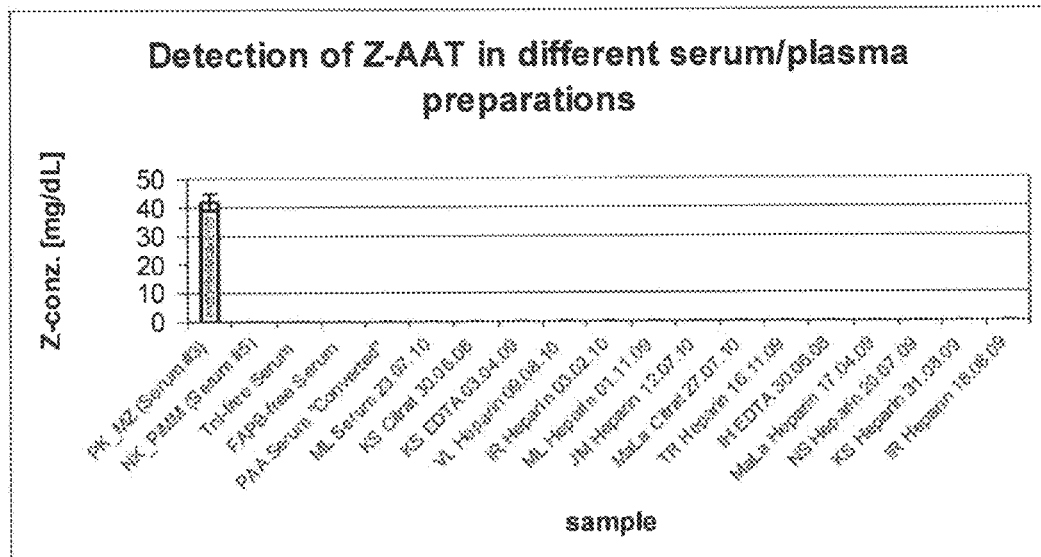
FIG. 14 shows determination of Z-AAT-concentration in different commercially available and in-house serum/plasma samples using PiZZ-ELISA.
Figure 15A:
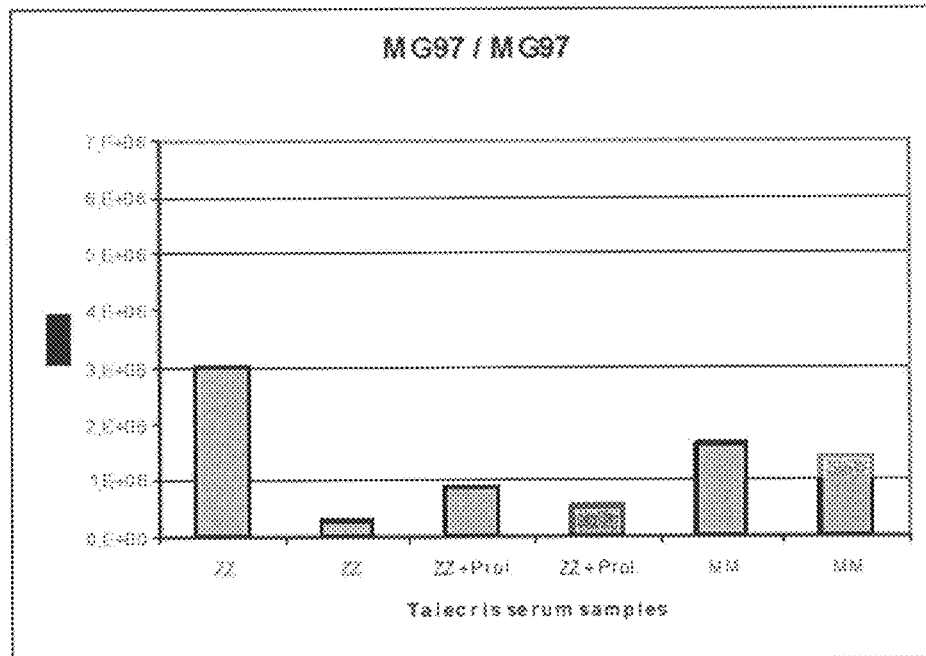
FIGS. 15A-15D show testing serum samples #1-6 in every possible antibody combination, whereby the antibody mentioned first is the capture antibody immobilized on the nitrocellulose, the antibody mention after the slash is the detector antibody coupled to the gold particles.
Figure 15B:
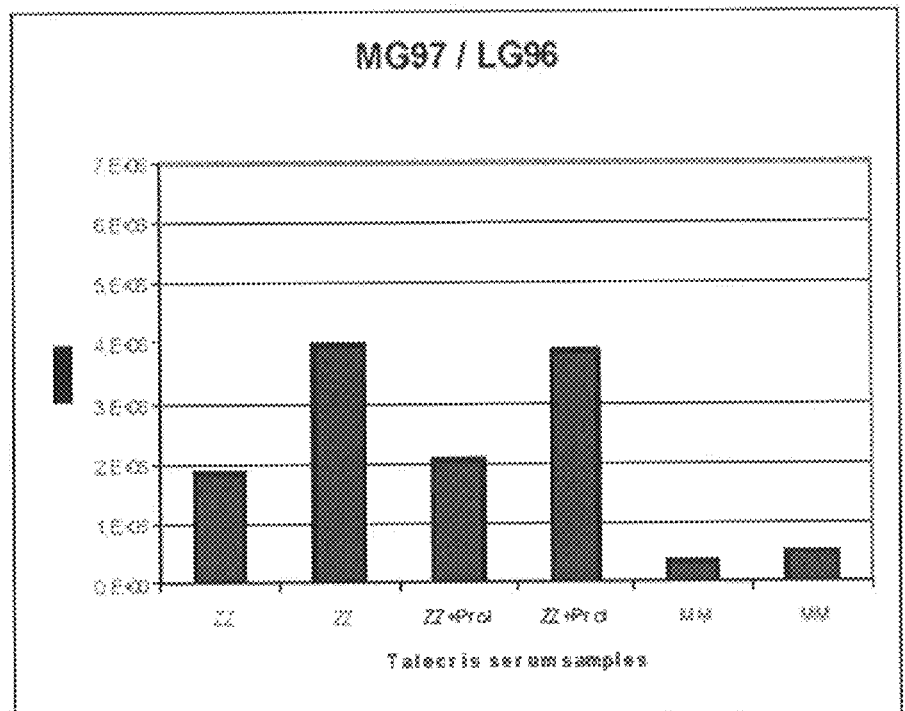
Figure 15C:
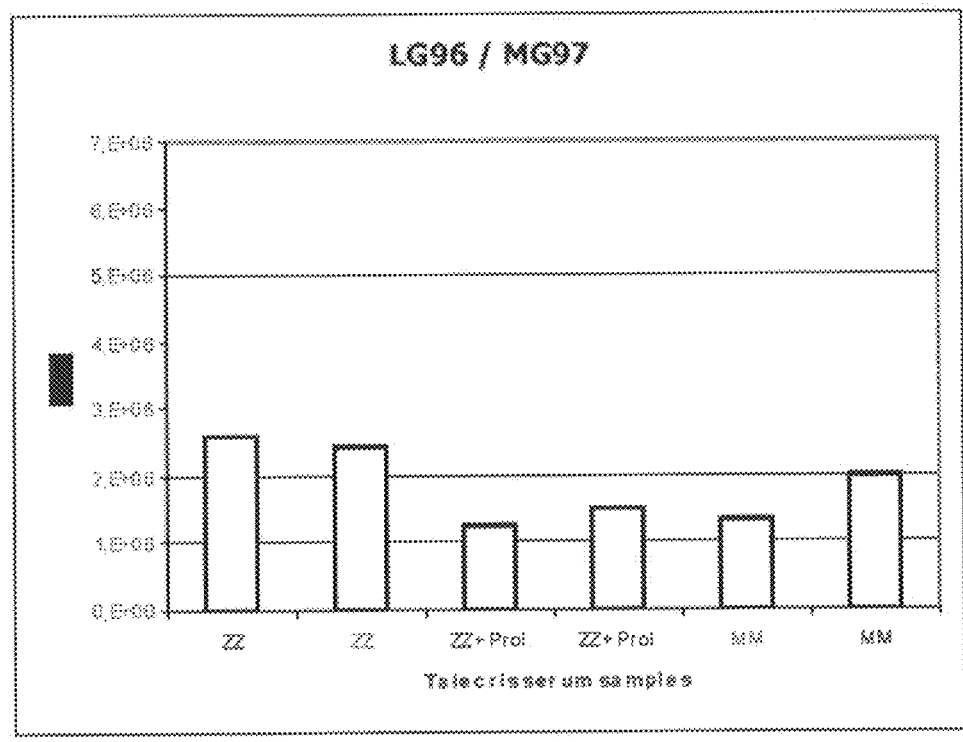
Figure 15D:
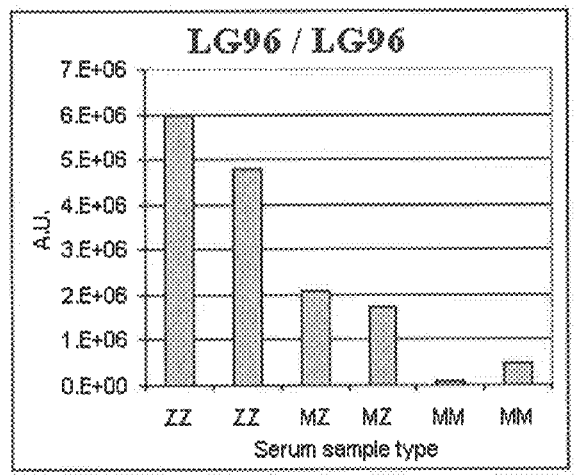

The specificity of the antibodies MG97 and LG96 was confirmed. Serum samples #5 and 6 were clearly negative, but serum samples #1-4 showed a strong positive signal. Different serum and plasma preparations, commercially available or in-house preparations, were tested for their Z-AAT-content (FIG. 14). Commercially available serum/plasma samples, as well as in-house samples, can be used as negative samples.

Antibody Labeling

The MG97 as well as the LG96 antibody was successfully coupled to 40 nm colloidal gold particles.

Antibody Combination

The antibodies were used as capture antibody as well as detector antibody in every possible combination. Serum samples #1-6 were used for the antibody screening. (FIGS. 15A-15D).

Conclusion

The combinations MG97/LG96 and LG96/LG96 (capture antibody/detector antibody) were identified as best in terms of differentiation between positive samples (#1-4) and negative samples (#5 and 6). The LG96/LG96 combination may be preferable because the results from #1+2, 3+4 and 5+6 were closer together.

Example 5

Device Testing

Figure 26:
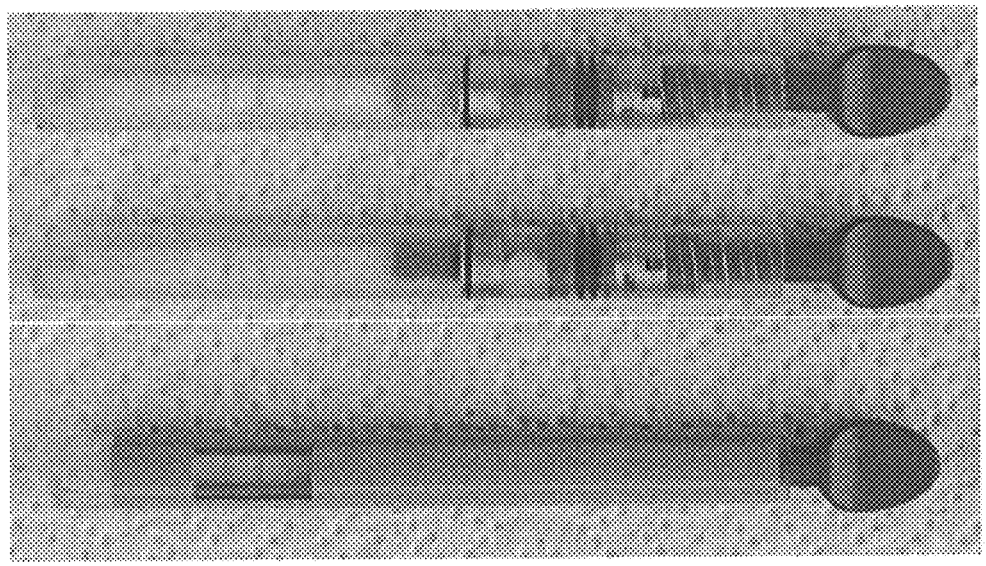
FIG. 26 shows the results of three separate screenings of ZZ(+) serum samples using one embodiment of a device of the present invention.
Figure 27:
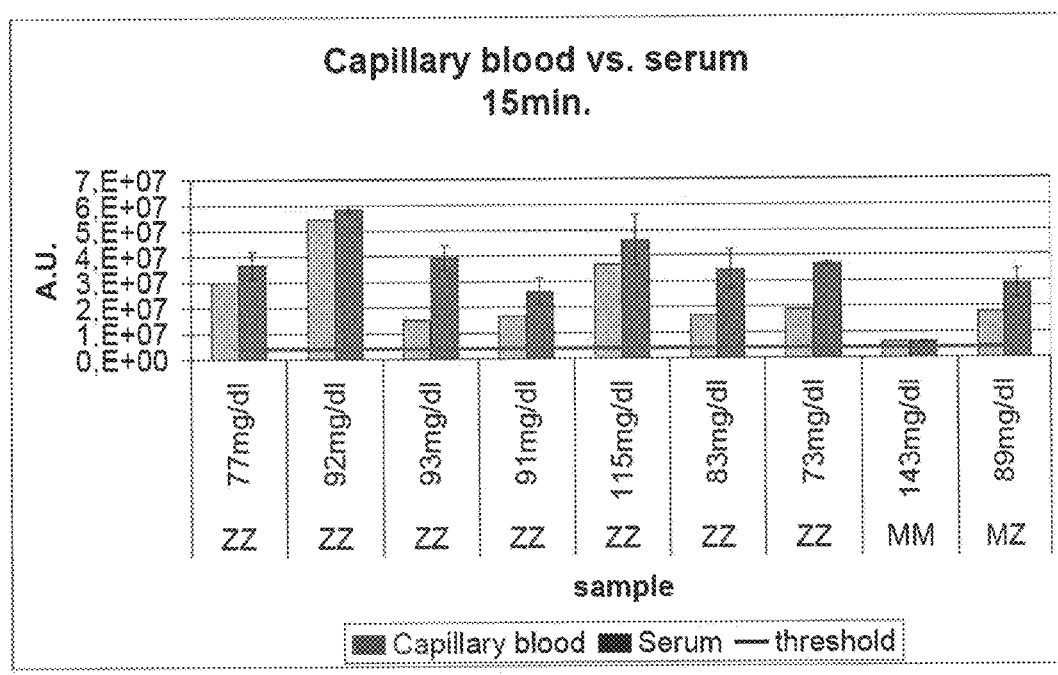
FIG. 27 shows testing capillary blood versus serum samples (comparison of 20 µl capillary blood and serum sample from the same donor). Test signals were measured after 15 minutes using an optical reader (QuickSens Omega 100 reader). Numbers in mg/dL indicates the AAT serum levels determined by nephelometry.
Figure 28:
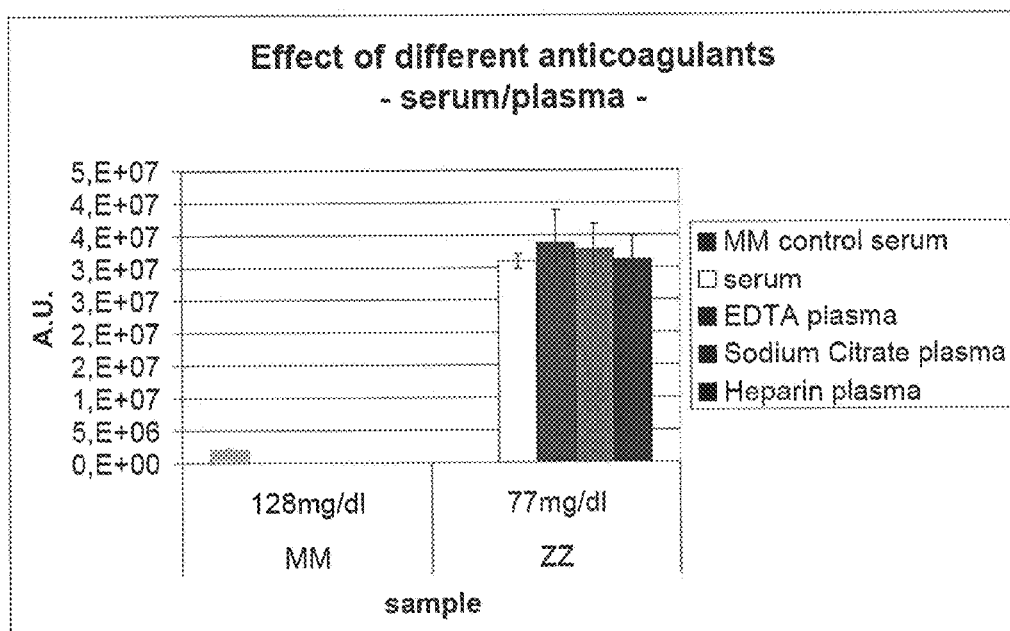
FIG. 28 shows effect of different anticoagulants on test results. Control: M-serum. Test samples: ZZ-EDTA plasma, ZZ-Citrate plasma, and ZZ-Heparin plasma. Test Signals were measured an optical reader 15 minutes after starting the test. Numbers in mg/dL indicates the AAT serum levels determined by nephelometry.
Figure 29:
FIG. 29 shows testing serum samples from: (A) MM donor; (B) ZZ donor; and (C) SZ donor (20 µl serum samples were used and results shown after different times). 'Vol.' is signal intensity of the test line (T) measured by an optical reader. Control line is designated by 'C'
Figure 30:
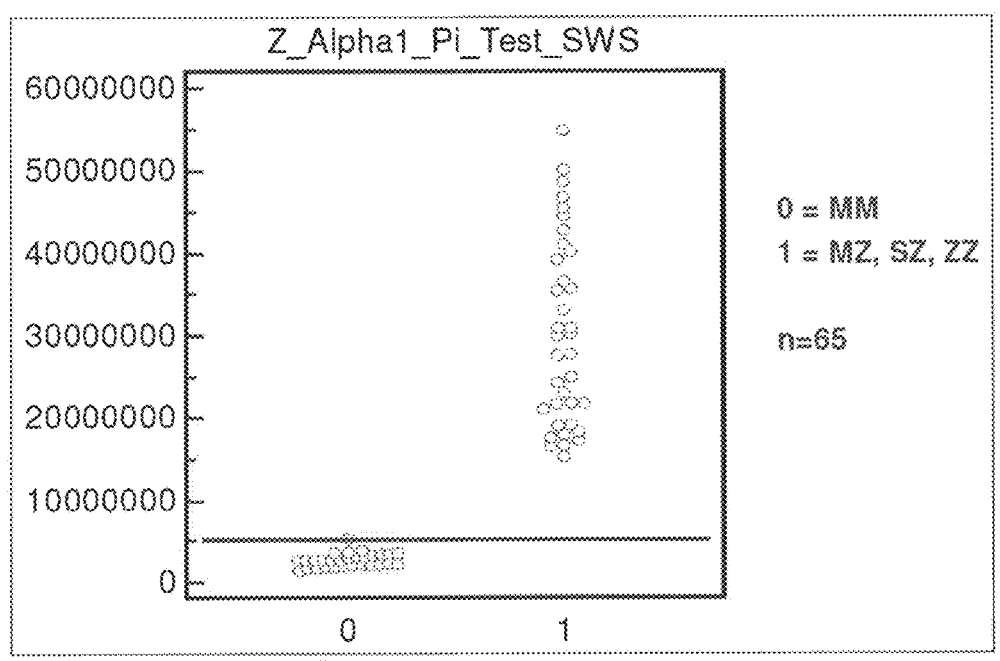
FIG. 30 shows testing summary of n-65 tests with serum and whole blood. 0=PiMM samples; 1=PiMZ, PiSZ, and PiZZ samples. Test signals were measured after 15-20 minutes using an optical reader.

ZZ(+) serum was tested in three separate devices as shown in FIG. 26. All 3 tests were positive.

What is claimed:

1. An immunoassay device comprising: a membrane having an alpha-1 antitrypsin protein comprising the Z-mutation (Z-AAT proteins) capture area defined by a capture antibody immobilized thereto, wherein the capture antibody is LG96, MG97, or comprises an antigen-binding fragment of either LG96 or MG97.

2. The device of claim 1, further comprising a sample application area and a flow path from the sample application area to the Z-AAT protein capture area, wherein the presence or amount of a Z-AAT protein in a fluid sample can be determined by formation of a complex between the capture antibody and the Z-AAT protein that may be present in the fluid sample.

3. The device of claim 2, further comprising a conjugate structure located in the flow path, wherein the conjugate structure comprises a detection reagent specific for the Z-AAT protein, the detection reagent being mobile or mobilizable.

4. The device of claim 3, wherein the detection reagent comprises a detector antibody.

5. The device of claim 4, wherein the detector antibody is LG96 or an antigen-binding fragment thereof.

6. The device of claim 4, wherein the detector antibody is MG97 or an antigen-binding fragment thereof.

7. The device of claim 4, wherein the detector antibody is labeled with a reporter moiety.

8. The device of claim 4, wherein the detector antibody is a gold-conjugated detector antibody.

9. The device of claim 2, wherein a source of the fluid sample is capillary blood, serum, or plasma.

10. An immunoassay device for determining the presence or amount of an alpha-1 antitrypsin protein comprising the Z-mutation (Z-AAT protein) in a fluid sample, the device comprising:
a sample application area;
a microporous membrane having a Z-AAT protein capture area defined by a capture antibody immobilized thereto, wherein the capture antibody is LG96 or antigen-binding fragment thereof;
a flow path from the sample application area to the Z-AAT protein capture area, wherein the presence or amount of a Z-AAT protein in a fluid sample can be determined by formation of a complex between the capture antibody and the Z-AAT protein that may be present in the fluid sample; and
a conjugate structure located in the flow path, wherein the conjugate structure comprises a detection reagent specific for the Z-AAT protein, the detection reagent being mobile or mobilizable, wherein the detection reagent is gold-conjugated LG96 or a gold-conjugated antigen-binding fragment thereof.

11. A method for detecting a Z-AAT protein in a subject, the method comprising:
applying a biological sample from the subject to the immunoassay device of claim 10; and
detecting a complex that is formed between the capture antibody and the Z-AAT protein that may be present in the fluid sample, wherein detection of the complex indicates the presence of the Z-AAT protein in the sample.

12. The device of claim 1, further comprising:
a sample application area;
a flow path from the sample application area to the Z-AAT protein capture area, wherein the presence or amount of a Z-AAT protein in a fluid sample can be determined by formation of a complex between the capture antibody and the Z-AAT protein that may be present in the fluid sample; and
a conjugate structure located in the flow path, wherein the conjugate structure comprises a detection reagent specific for the Z-AAT protein, the detection reagent being mobile or mobilizable, wherein the detection reagent is gold-conjugated LG96 or a gold-conjugated antigen-binding fragment of LG96.

13. The device of claim 12, wherein the capture antibody is LG96 or an antigen-binding fragment of LG96.

* * * * *